(12) United States Patent
Ratan et al.

(10) Patent No.: US 9,505,741 B2
(45) Date of Patent: Nov. 29, 2016

(54) PROLYLHYDROXYLASE INHIBITORS AND METHODS OF USE

(75) Inventors: Rajiv R. Ratan, Scarsdale, NY (US); Irina Gazaryan, White Plains, NY (US); Natalya Smirnova, White Plains, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 13/579,646

(22) PCT Filed: Feb. 17, 2011

(86) PCT No.: PCT/US2011/025188
§ 371 (c)(1),
(2), (4) Date: Oct. 2, 2012

(87) PCT Pub. No.: WO2011/106226
PCT Pub. Date: Sep. 1, 2011

(65) Prior Publication Data
US 2013/0023528 A1   Jan. 24, 2013

Related U.S. Application Data

(60) Provisional application No. 61/307,276, filed on Feb. 23, 2010, provisional application No. 61/305,420, filed on Feb. 17, 2010.

(51) Int. Cl.
| | |
|---|---|
| *A61K 31/40* | (2006.01) |
| *A61K 31/4709* | (2006.01) |
| *C07D 401/12* | (2006.01) |
| *A61K 31/404* | (2006.01) |
| *C07D 209/18* | (2006.01) |

(52) U.S. Cl.
CPC ........... *C07D 401/12* (2013.01); *A61K 31/404* (2013.01); *A61K 31/4709* (2013.01); *C07D 209/18* (2013.01)

(58) Field of Classification Search
None
See application file for complete search history.

(56) References Cited

U.S. PATENT DOCUMENTS

| | | | |
|---|---|---|---|
| 8,138,356 B2 * | 3/2012 | Chaudhary | ........ A01K 67/0271 549/49 |
| 2004/0147570 A1 | 7/2004 | Gerlach et al. | |
| 2005/0043248 A1 | 2/2005 | Lewis et al. | |
| 2008/0293699 A1 | 11/2008 | Reed et al. | |

FOREIGN PATENT DOCUMENTS

| | | |
|---|---|---|
| WO | 2008/024922 A2 | 2/2008 |
| WO | WO 2008/014602 A1 | 2/2008 |
| WO | WO 2008014602 A1 * | 2/2008 |
| WO | 2009/070644 A1 | 6/2009 |
| WO | WO 2009137597 A1 * | 11/2009 ........... A61K 31/351 |
| WO | 2009/151972 A1 | 12/2009 |
| WO | WO 2011-085126 A2 | 7/2011 |
| WO | 2011/146618 A1 | 11/2011 |

OTHER PUBLICATIONS

Kalaria, "The role of cerebral ischemia in Alzheimer's disease," Neurobiol Aging. Mar.-Apr. 2000;21(2):321-30.*
English-language Translation of Chinese Office Action dated May 13, 2014 received from related Chinese Application No. 201180020425.3.
Chinese Office Action dated May 3, 2016 issued in Corresponding Chinese Patent Application No. 201410821107.2, and an English Translation thereof.
Anary-Abbasinejad M. et al., "P2O5-Hexamethyldisiloxane (HMDS): An Efficient System to Induce the Three-Component Reaction of Enolic Systems, Aromatic Aldehydes, and Acetonitrile", Synthetic Communications 38 (21):3706-3716 (Oct. 2008).
Bachand B. et al., "Potent and Selective Bicyclic Lactam Inhibitors of Thrombin. Part 4: Transition State Inhibitors", Bioorganic & Medicinal Chemistry Letters 11(3):287-290 ( Feb. 2001).
Blinnikov A.N. et al., "a-Hydroxyalkyl(Benzyl)Furazans and a-Hydroxyalkyl(Benzyl)Furoxans. Synthesis and Reactivity", Russian Chemical Bulletin 45(7):1692-1698 (1996), Database Accession No. 7766766, XP-002714461.
Henkel B. et al., "A New and Efficient Multicomponent Solid-Phase Synthesis of 2-Acylaminomethylthiazoles", Tetrahedron Letters 44(18):3679-3682 (Apr. 2003).
Jang J.Y. et al., "Synthesis of 4,5,6,7-Tetrahydroisoxazolo[3,4-c]Pyridines and Their Antifungal Activities", Heterocycles 53(11):2391-2402 (2000), Database Accession No. 8155987, XP-002714462.
Kobayashi K. et al., "A Convenient Synthesis of 3-(1-Aminoalkyl)Quinolin-2(1H)-One Derivatives", Synthesis 16 (1):2673-2676 (Jan. 2005).
Mosslemin M.H. et al., "A Clean Synthesis of Oxazino[5,6-F]Quinolinone and Naphtho[1,2-E)Oxazinone Derivatives", Monatsch Chem 139(10):1247-1250 (Apr. 2008).
Smirnova N.A. et al., "Utilization of an In Vivo Reporter for High Throughput Identification of Branched Small Molecule Regulators of Hypoxic Adaptation", Chemistry & Biology 17(4)380-391 (Apr. 23, 2010).
Stankovicova H. et al., "Reaction of 4-Oxochromene-3-Carboxaldehydes With Primary Amides and Benzotriazole or 1H-1,2,4-Triazole" Collection of Czechoslovak Chemical Communications 62(5):781-790 (1997), Database Accession No. 7886827, XP-002714463.
Warshakoon N.C. et al., "Structure-Based Design, Synthesis, and SAR Evaluation of a New Series of 8-Hydroxyquinolines as HIF-1a Prolyl Hydroxylase Inhibitors", Bioorganic & Medicinal Chemistry Letters 16 (21):5517-5522 (Nov. 2006).
Pirrone, Gazzetta Chimica Italiana 71:320, 325 (1941), Database Accession No. 355576, XP-002714466.
Pirrone, Gazzetta Chimica Italiana 70:520, 523 (1940), Database Accession No. 370896, XP-002714467.

(Continued)

*Primary Examiner* — Jared D Barsky
(74) *Attorney, Agent, or Firm* — Scully Scott Murphy & Presser

(57) ABSTRACT

Compounds for inhibiting hypoxia inducible factor (HIF) prolyl-4-hydroxylases (PHDs) having the general formula (1). Methods of using these and related compounds for treating a patient having a condition that would benefit from inhibiting HIF PHD are also described herein.

7 Claims, 25 Drawing Sheets

(56) References Cited

OTHER PUBLICATIONS

Supplementary Partial European Search Report dated Oct. 28, 2013 received from related European Application No. 11747882.6.
Mikhaylova O. et al., "The Von Hippel-Lindau Tumor Suppressor Protein and Egl-9-Type Proline Hydroxylases Regulate the Large Subunit of RNA Polymerase II in Response to Oxidative Stress", *Molecular and Cellular Biology* 28(8):2701-2717 (Apr. 2008).
Xie L. et al., "Oxygen-Regulated $\beta_2$-Adrenergic Receptor Hydroxylation by EGLN3 and Ubiquitylation by pVHL", *Science Signaling* 2(78):1-10 (Jul. 7, 2009).
Safran M. et al., "Mouse Model for Noninvasive Imaging of HIF Prolyl Hydroxylase Activity: Assessment of an Oral Agent that Stimulates Erythropoietin Production", *PNAS* 103(1):105-110 (Jan. 3, 2006).
International Search Report dated Nov. 25, 2011 received from the Korean Intellectual Property Office from related International Application No. PCT/US2011/025188.
Database Registry [Online] Chemical Abstracts, Accession No. 353519-27-4, XP-002737758 (Aug. 29, 2001).
Database Registry [Online] Chemical Abstracts, Accession No. 354785-76-5, XP-002737759 (Sep. 5, 2001).
Database Registry [Online] Chemical Abstracts, Accession No. 1961:33086, XP-002737760 (1960).
Sen A.B. et al., "Reaction of Aldehydes and Amines With 8-Hydroxyquinaldine and 8-Qunolinol", Journal of the Indian Society 37(10):640-642 (1960), XP-009183411.
Database Registry [Online] Chemical Abstracts, Accession No. 385786-48-1, XP-002737761 (Jan. 24, 2002).
Database Registry [Online] Chemical Abstracts, Accession No. 430457-95-7, XP-002737762 (Jun. 14, 2002).
Database Registry [Online] Chemical Abstracts, Accession No. 496837-91-3, XP-002737763 (Mar. 4, 2003).
Database Registry [Online] Chemical Abstracts, Accession No. 304685-32-3, XP-002737764 (Nov. 28, 2000).
Database Registry [Online] Chemical Abstracts, Accession No. 664977-40-6, XP-002737765 (Mar. 19, 2004).
Database Registry [Online] Chemical Abstracts, Accession No. 315697-86-0, XP-002737766 (Jan. 22, 2001).
Database Registry [Online] Chemical Abstracts, Accession No. 292057-76-2, XP-002737767 (Oct. 2, 2000).
Database Registry [Online] Chemical Abstracts, Accession No. 332173-76-9, XP-002737768 (Apr. 24, 2001).
Database Registry [Online] Chemical Abstracts, Accession No. 333314-85-5, XP-002737769 (Apr. 27, 2001).
Extended European Search Report dated Apr. 14, 2015 received from Application No. 15 15 0104.6.

* cited by examiner

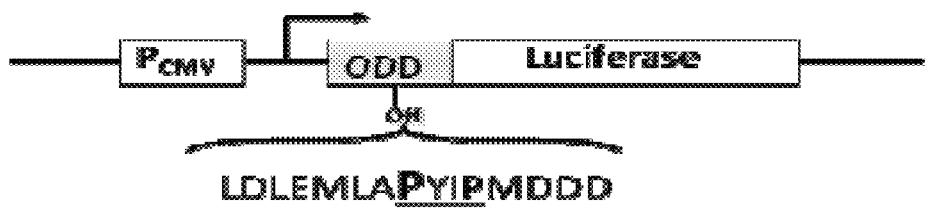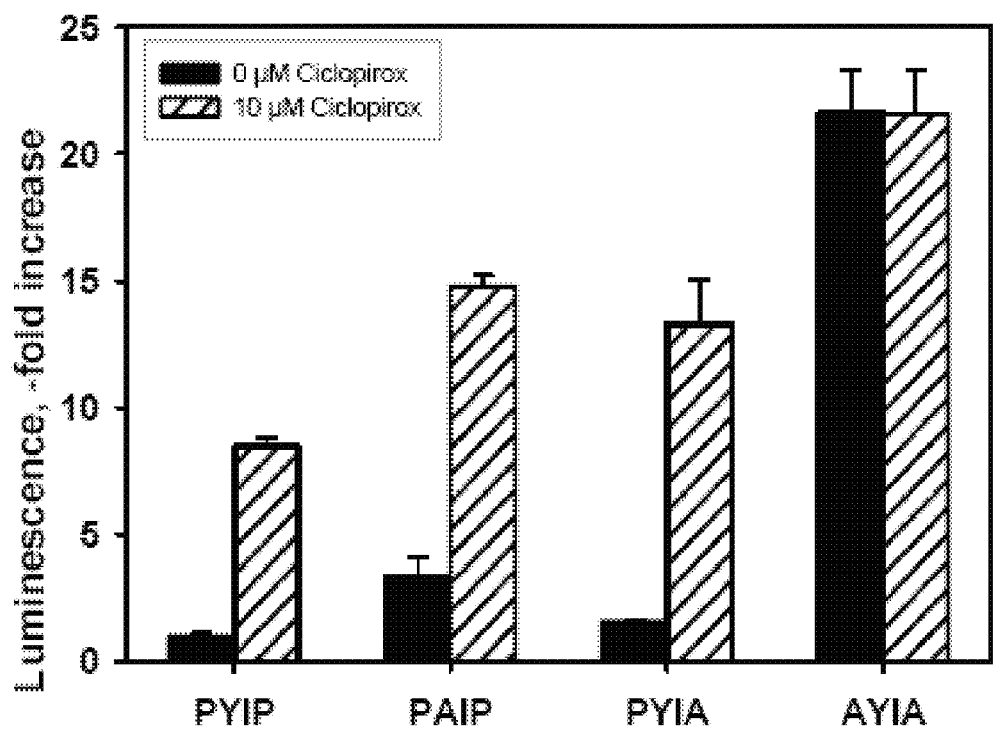
FIG. 2

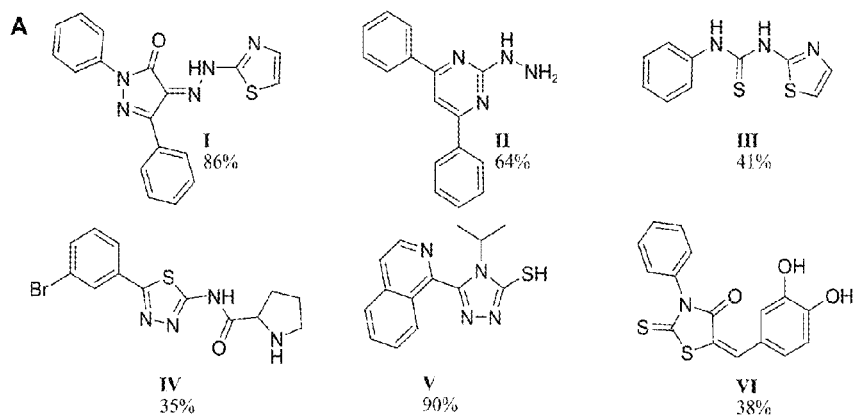
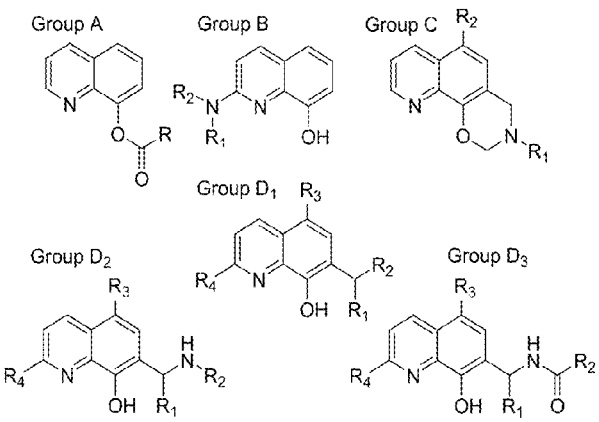
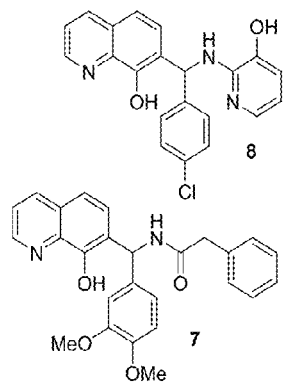
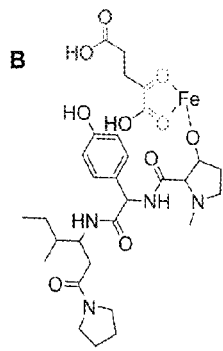
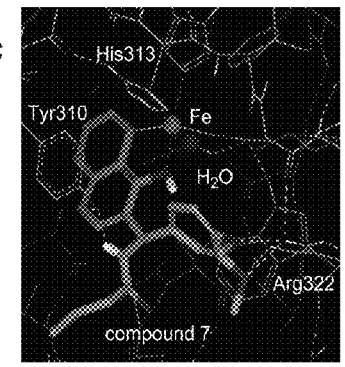
FIG. 4

(A)

(B)

(C)

| Compound Group & Number | $R_1$ | $R_2$ | $R_3$ | $R_4$ | Max Activ -fold | $IC_{50}$, μM | "Lag", μM | $K_{Fe}$, μM | $k_a$, $M^{-1}s^{-1}$ |
|---|---|---|---|---|---|---|---|---|---|
| Ciclo-pirox | | | | | 8.5±0.5 | 4.5±0.5 | 2±0.5 | 0.08±0.02 | 300±50 |
| Oxyqui-noline | | | | | 4.5±0.3 | 10±1 | 4±0.5 | 0.20±0.05 | 110±20 |
| D1, #10 | pyridin-4-yl | piperidin-1-yl | H | H | 5.0±0.4 | 10±1 | 1.8±0.2 | 0.08±0.02 | 250±50 |
| D2, #9 | pyridin-3-yl | pyridin-2-yl | H | CH₃ | 5.5±0.5 | 10±1 | 5±0.2 | 0.78±0.18 | 30±5 |
| D2, #12 | pyridin-2-yl | 6-methyl-pyridin-2-yl | H | CH₃ | 6.0±0.5 | 4.5±0.5 | 3±0.4 | 0.20±0.05 | n.d. |
| D2, #5 | Ph | pyridin-2-yl | H | CH₃ | 5.2±0.3 | 7±0.2 | 5±0.5 | 1.50±0.30 | 20±3 |
| D2, #8 | p-Cl-Ph | 3-hydroxy-pyridin-2-yl | H | H | 7.0±0.2 | 2±0.3 | 0.6±0.1 | 0.19±0.04 | 110±20 |
| D2, #3 | m,p-(CH₃O)₂-Ph | pyridin-2-yl | H | CH₃ | 2.0±0.3 | 12±0.5 | 10±0.5 | 0.80±0.20 | 20±3 |
| D2, #13 | m,p-(CH₃O)₂-Ph | 4-methyl-pyridin-2-yl | H | CH₃ | 6.0±0.2 | 7±0.2 | 5±0.5 | 0.10±0.02 | n.d. |
| D2, #2 | m,p-(OCH₂O)-Ph | 6-methyl-pyridin-2-yl | H | CH₃ | 4.5±0.5 | 12±1 | 7±0.5 | 0.10±0.02 | n.d. |
| D3, #1 | m,p-(CH₃O)₂-Ph | butyl | H | H | 7.0±0.2 | 2.6±0.2 | 1±0.1 | 0.11±0.02 | 240±40 |
| D3, #4 | m,p-(CH₃O)₂-Ph | 1-iso-butyl | H | H | 6.8±0.2 | 2.1±0.2 | 0.6±0.2 | 0.10±0.02 | 210±40 |
| D3, #7 | m,p-(CH₃O)₂-Ph | benzyl | H | H | 7.0±0.2 | 2.2±0.2 | 1±0.1 | 0.10±0.02 | 180±35 |
| D3, #6 | m-NO₂-Ph | butyl | H | H | 7.2±0.3 | 4±0.1 | 1.8±0.2 | 0.20±0.04 | 95±15 |
| D3, #11 | m,p-(OCH₂O)-Ph | ethyl | NO₂ | H | 4.0±0.3 | 12±1 | 8±1 | 0.15±0.03 | 100±20 |

FIG. 7

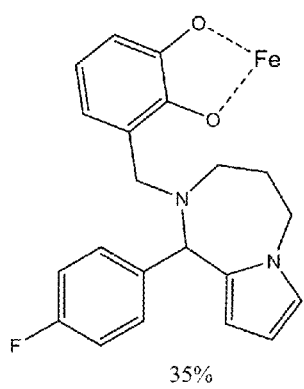
35%
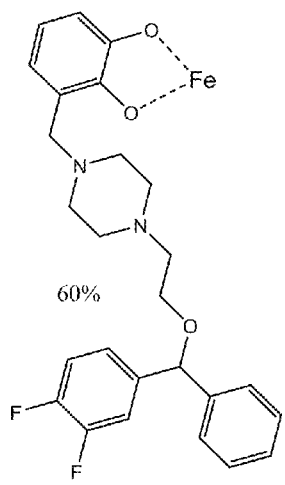
60%
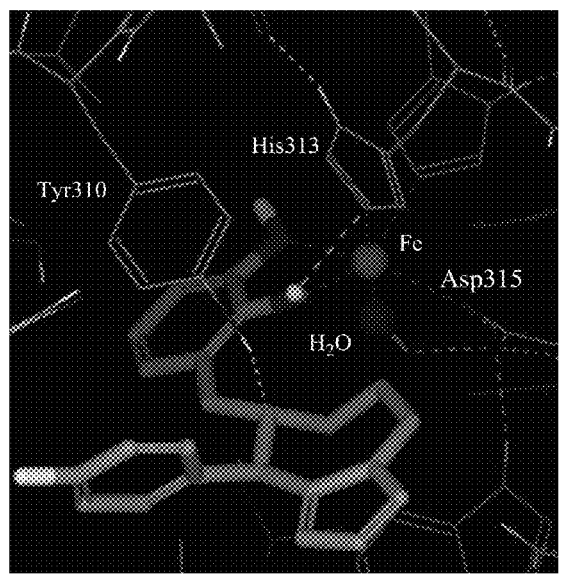
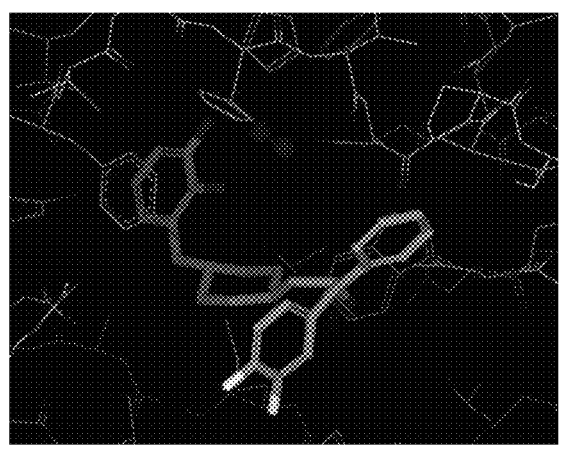
FIG. 9

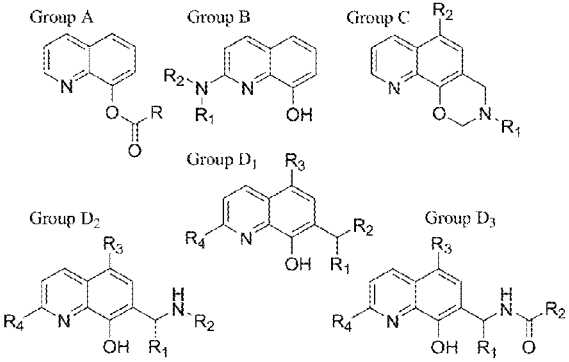

| Compound Group & Number | R₁ | R₂ | R₃ | R₄ | Activation (%) |
|---|---|---|---|---|---|
| Ciclopirox | | | | | 100 |
| Oxyquinoline | | | | | 54 |
| (A) | furan-2-yl | | | | 38 |
| (A) | p-4-Cl-benzenesulfonyl-Ph | | | | 26 |
| (B) | pyridin-2-yl | H | | | 48 |
| (B) | 8-hydroxyquinolin-2-yl | butyl | | | 85 |
| (C) | 2,2,6,6-Tetramethyl-piperidin-4-yl | Cl | | | 70 |
| (C) | pyridine-3-ylmethyl | Cl | | | 142 |
| (C) | 2-morpholin-4-yl-ethyl | Cl | | | 114 |
| (C) | 1-phenyl-ethyl | Cl | | | 157 |
| (C) | 2-cyclohex-1-enyl-ethyl | Cl | | | 110 |
| (C) | 1,1-dioxo-tetrahydrothiophen-3-yl | Cl | | | 96 |
| (D1) | H | H | CH₃ | CH₃ | 0 |
| (D1) | H | H | CH₃ | H | 86 |
| (D2) | Ph | pyridin-2-yl | H | H | 127 |
| (D2) | pyridin-4-yl | pyridin-2-yl | H | H | 124 |
| (D2) | pyridin-4-yl | pyrrolidin-1-yl | H | H | 106 |
| (D2) | pyridin-4-yl | 1-morpholin-4-yl | Cl | H | 115 |
| (D2) | pyridin-2-yl | 1-morpholin-4-yl | H | H | 4 |
| (D2) | thiophen-2-yl | pyridin-2-yl | H | H | 60 |
| #8 (D2) | p-Cl-Ph | 3-hydroxy-pyridin-2-yl | H | H | 130 |
| (D3) | o-MeO-Ph | propyl | H | H | 126 |
| (D3) | m,p-(MeO)₂-Ph | propyl | H | H | 125 |
| (D3) | m-NO₂-Ph | propyl | H | H | 121 |
| (D3) | furan-2-yl | propyl | H | H | 105 |

FIG. 10

PROLYLHYDROXYLASE INHIBITORS AND METHODS OF USE

CROSS REFERENCE TO RELATED APPLICATION

This application claims the benefit of priority from U.S. Provisional Application No. 61/307,276, filed on Feb. 23, 2010, and U.S. Provisional Application No. 61/305,420, filed on Feb. 17, 2010.

GOVERNMENT SUPPORT

This invention was made with Government support under Grant Number 1R43CA133985-01 awarded by the National Institutes of Health. The United States Government has certain rights in the invention.

FIELD OF THE INVENTION

The invention relates to branched inhibitors of hypoxia inducible factor (HIF) prolyl-4-hydroxylases (PHDs) and methods of using these inhibitors for inhibiting prolylhydroxylase enzyme activity for the prevention and treatment of human conditions where disease results from suppressed or delayed onset of the cellular HIF response, where the conditions include, for example, ischemia, retinal degeneration, and anemia. The invention is also directed to methods for using these inhibitors to protect cells or tissue from hypoxic damage for the purpose of, for example, organ transplantation, ischemic preconditioning, or stem cell transplantation.

BACKGROUND OF THE INVENTION

Ischemia is the decrease in blood supply to an organ due to defects in the vasculature carrying blood to such organ. Ischemia results in hypoxia, as oxygen is supplied through organ blood perfusion. The effects of hypoxia may be detrimental to the long-term function of the affected organ, as cell death occurs with sustained hypoxia. Moreover, ischemia may be lethal. Ischemia can result from, for example, cardiovascular disease in stroke and myocardial infarction, acute kidney injury, cerebral trauma, in association with neurodegeneration, as well as from anti-cancer therapy.

Hypoxia is a common etiology of cell injury in human disease, including stroke, myocardial infarction, and solid tumors. Over the past two decades, cell adaptation to hypoxia has emerged as a well-defined active process. Each cell of a multicellular organism can respond to hypoxia by building up hypoxia inducible factor (HIF), a ubiquitous transcription factor capable of activating a battery of genes including genes involved in glucose uptake and metabolism, extracellular pH control, angiogenesis, erythropoiesis, mitogenesis, and apoptosis. The discovery of HIF opened new horizons for the treatment of ischemia and cancer: upregulation of HIF levels has been shown to be beneficial for ischemic diseases, stem cell proliferation [Zhang, C. P., et al., Neurosignals 15, 259-265 (2006)] and transplantation [Liu, X. B., et al., J Cell Biochem 106, 903-911 (2009)], while down-regulation of elevated HIF, a marker of most aggressive cancers, represents a new approach for cancer treatment.

HIF consists of two subunits HIF-1α and HIF-1β, among which HIF-1α is rapidly degraded under normoxic conditions, while HIF-1β is stable [Wang, G. L., et al., Proc Natl Acad Sci USA 92, 5510-5514 (1995); Wang, G. L., et al., J Biol Chem 270, 1230-1237 (1995)]. HIF levels are regulated primarily by post-translational modification of conserved proline residues. Hydroxylation of Pro564 and/or 402 residues in HIF-1α is a prerequisite for its interaction with the von Hippel-Lindau (VHL) protein, yielding a complex that provides HIF ubiquitinylation and subsequent proteasomal degradation [Kaelin, W. G., Jr., Biochem Biophys Res Commun 338, 627-638 (2005)]. Hydroxylation of Pro564 occurs prior to Pro402 [Chan, D. A., et al., Mol. Cell. Biol. 25, 6415-6426 (2005)], although some experiments contradict this finding [Villar, D., et al., Biochem J 408, 231-240 (2007)]. Hydroxylation of HIF-1α Arg803 blocks its interaction with transcriptional proactivator p300 [Lando, D., et al., Science 295, 858-861 (2002)]. In both cases, HIF hydroxylation is executed by α-KG-dependent non-heme iron dioxygenases, HIF prolyl-4-hydroxylase (PHD1-3 isozymes) and asparaginyl hydroxylase (or the so-called FIH, factor inhibiting HIF) [Hirota, K., et al., Biochem Biophys Res Commun 338, 610-616 (2005)].

HIF1 also upregulates a number of prodeath proteins, and thus, HIF1 upregulation can be either prodeath or prosurvival. However, recent evidence [Siddiq, A., et al., J Biol Chem 280, 41732-41743 (2005); Knowles, H. J., et al., Circ Res 95, 162-169 (2004); Baranova, O. et al., J Neurosci 27, 6320-6332 (2007)] strongly suggests that PHDs and FIH are important targets for medical intervention for a number of conditions including chronic anemia and stroke. PHD inhibitors abrogate the ability of HIF1-mediated transactivation of BNIP3 and PUMA to potentiate oxidative death in normoxia [Aminova, L., et al., Antioxidant & Redox Signaling 10, 1989-1998 (2008)]. Although new targets for intervention in the HIF pathway are constantly emerging, the latter observation justifies the search for PHD inhibitors rather than for other types of HIF activators. New substrates have been recently identified for PHD1 (e.g., Rpb1, large subunit of RNA polymerase II [Milchaylova, O., et al., Mol Cell Biol 28, 2701-2717 (2008)] responsible for the fundamental enzymatic activity of the complex, synthesizing all cellular mRNAs) and PHD3 (e.g., β2-adrenergetic receptor [Xie, L., et al., Science Signaling 2, 1-10 (2009)], whose sustained down-regulation is associated with heart failure and asthma) placing HIF PHDs into the focus of drug development efforts. Despite characterization of HIF PHDs as a potential target for anti-ischemic therapy, there has been very little progress in identifying lead compounds that function as HIF PHD inhibitors.

SUMMARY OF THE INVENTION

In a first aspect, the present invention is directed to several classes and specific types of compounds useful as HIF PHD inhibitor compounds. The compounds generally include an iron-binding portion attached to a branched portion, particularly wherein the branched portion includes a branched amino or amido moiety, as shown in Formula (1) below. In a second aspect, the present invention is directed to methods for treating a patient having a condition that would benefit from inhibiting HIF PHD in a patient by administering to the patient an effective amount of the HIF PHD-inhibiting compound.

In particular embodiments, the HIF PHD-inhibiting compound has a structure according to the following general formula:

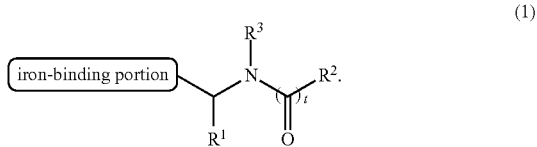

(1)

In Formula (1), the iron-binding portion has a chemical structure that includes at least one iron-binding functional group selected from carboxylic acid, carboxylic ester, keto, amino, amido, imino, ureido, nitro, hydroxy, nitrile, and amine oxide, wherein the iron-binding portion contains at least three and up to twenty carbon atoms. $R^1$ is a monocyclic group optionally substituted with one or more groups selected from —$R^4$, —C(O)$R^4$, —N$R^4{}_2$, —O$R^4$, —NO$_2$, —C(O)N$R^4{}_2$, —N$R^4$C(O)$R^4$, —C(O)O$R^4$, —N$R^4$C(O)N$R^4{}_2$, —N$R^4$C(O)O$R^4$, —SO$_2R^4$, nitrile, and halogen atom, wherein $R^4$ is, independently, hydrogen atom or a non-cyclic hydrocarbon group containing up to nine carbon atoms; and/or the monocyclic group is optionally substituted with one or more linkers linking the monocyclic group with the shown carbon atom, wherein the linker is selected from —$R^4$—, —C(O)—, —C(O)$R^4$—, —N$R^4$—, —C=N$R^4$—, —N=N$R^4$—, —C=N$R^4$—, —C=N—N$R^4$—, —O—, —S—, —C(O)N$R^4$—, —N$R^4$C(O)$R^4$—, —C(O)O—, —C(O)O$R^4$—, —N$R^4$C(O)N$R^4$—, —N$R^4$C(O)O$R^4$—, —SO$_2R^4$—, and combinations thereof. $R^2$ is selected from groups of $R^1$, as well as —$R^5$, —C(O)$R^5$, —N$R^5{}_2$, —O$R^5$, —NO$_2$, —C(O)N$R^5{}_2$, —N$R^5$C(O)$R^5$, —C(O)O$R^5$, —N$R^5$C(O)N$R^5{}_2$, —N$R^5$C(O)O$R^5$, —SO$_2R^5$, nitrile, and halogen atom, wherein $R^5$ is, independently, a cyclic or non-cyclic hydrocarbon group containing up to nine carbon atoms, optionally containing one or more ring-heteroatoms selected from nitrogen, oxygen, and sulfur, and/or one or more ring functional groups selected from —C(O)— and —C(S)—, and/or optionally substituted with one or more groups selected from —$R^4$, —C(O)$R^4$, —N$R^4{}_2$, —O$R^4$, —NO$_2$, —C(O)N$R^4{}_2$, —N$R^4$C(O)$R^4$, —C(O)O$R^4$, —N$R^4$C(O)N$R^4{}_2$, —N$R^4$C(O)O$R^4$, —SO$_2R^4$, nitrile, and halogen atom. $R^3$ is selected from hydrogen atom and hydrocarbon group containing up to six carbon atoms. Subscript t is a number of 0 or 1. Optionally, $R^2$ and $R^3$ are interconnected to form a ring. In particular embodiments, when the iron-binding portion is, or includes, a 8-hydroxyquinolin-7-yl ring system, the 8-hydroxyquinolin-7-yl ring system contains, at least or only on position 2 thereon, a polar group, particularly one selected from —C(O)OH, —OH, halogen atom, and nitro group, as well as methylene-linked versions thereof.

The instant invention made this discovery by adapting methodology previously used for visualization of HIF stabilization in transgenic mice [Safran, M., et al., PNAS, 2006, 103, 105-110 (2006)] for the purpose of high-throughput screening (HTS) of potential HIF PHD inhibitor compounds. In the method, the reporter system consists of the HIF-1α gene fragment encoding the oxygen degradable domain (ODD) containing the key proline residue followed by luciferase gene (luc). The regulation of luciferase protein stability in this reporter system is the same as the physiological activation of HIF: hydroxylation of oxygen-degradable domain (ODD, which contains 530-653 a.a. of HIF1-α), and results in recognition of the ODD-luc fusion protein by VHL followed by its ubiqutinylation and proteasomal degradation (FIG. 1A). As shown in further detail below, the approach proved to be productive for discovering new lead HIF PHD inhibitor compounds.

High-throughput screening of 85,000 compounds in search of HIF PHD inhibitors was performed. Several classes and specific types of compounds were found to be promising or efficacious, particularly those belonging to the group of branched 8-hydroxyquinoline derivatives whose binding mode into the active site of PHD2 resembles that of the HIF peptide. The biological effects of the newly identified hits, i.e. HIF1 protein stabilization, induction of HIF1-regulated genes such as erythropoietin (Epo), lactate dehydrogenase (LDHA) and phosphoglycerate kinase 1 (PGK1), neuroprotection in homocysteic acid (HCA) cellular model of oxidative stress, are all in good agreement with their activation effects in the reporter assay.

BRIEF DESCRIPTION OF THE FIGURES

FIG. 2. Effect of mutations adjacent to Pro564 on the reporter response to 10 µM ciclopirox, three hour incubation.

FIG. 4. New hit groups identified in HTS. A: Chemical structures of hits: (I), Edaravon-type hit: (Z)-1,3-diphenyl-4-(thiazol-2-yl-hydrazono)-1H-pyrazol-5(4H)-one (86%); (II), Hydralazine type hit: 2-hydrazinyl-4,6-diphenylpyrimidine (64%); (III), Dibenzoylmethane group hit: 1-phenyl-3-(1,3-thiazol-2-yl)thiourea (41%); (IV), Thiadiazole group hit: N-[5-(3-bromophenyl)-[1,3,4]thiadiazol-2-yl]pyrrolidine-2-carboxamide (35%); (V), Triazole group hit: 4-isopropyl-5-isoquinolin-1-yl-4H-[1,2,4]triazole-3-thiol (90%); (VI), Catechol group hit: (E)-5-(3,4-dihydroxybenzylidene)-3-phenyl-2-thioxothiazolidin-4-one (38%). B: Schematic presentation of docking mode of hydroxylated HIF peptide into PHD2; C: Docking of best hits, compounds 7 and 8, into PHD2.

FIG. 7. Table with comparison of reporter activation parameters and iron binding properties of branched oxyquinolines (structural subgroups D1-D3 as depicted in FIG. 4).

FIG. 9. Docking of two confirmed 2,3-dihyroxyphenyl-containing hits with a branching motif into PHD2, view to the entrance to the active site: top, 3-((1-(4-fluorophenyl)-4,5-dihydro-1H-pyrrolo[1,2-a][1,4]diazepin-2(3H)-yl)methyl)benzene-1,2-diol, 40% activation in HTS; bottom, 3-((4-(2-((3,4-difluorophenyl) (phenyl)methoxy)ethyl)piperazin-1-yl)methyl)benzene-1,2-diol, 60% activation in HTS.

FIG. 10. SAR based on the results of confirmed oxyquinoline hits from HTS.

DETAILED DESCRIPTION OF THE INVENTION

Figure 1A:
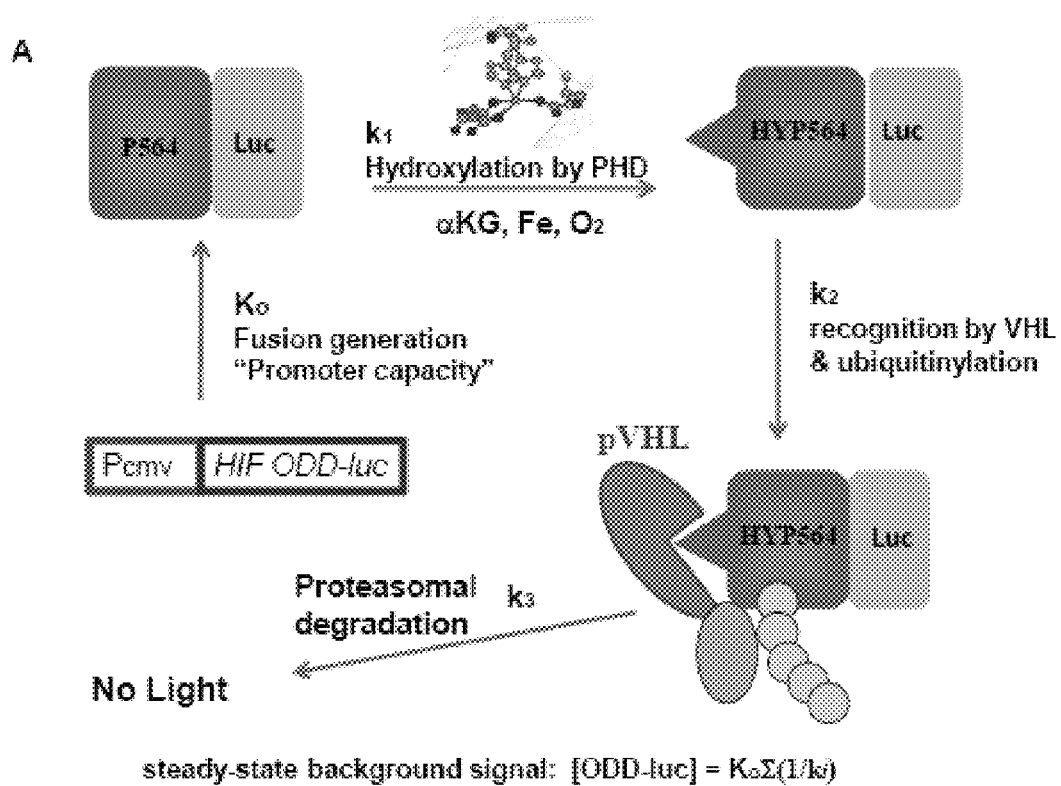
FIG. 1. Mechanism of reporter activation and response to canonical HIF PHD inhibitors: (A) Schematic presentation of reporter performance showing key steps/potential sites of inhibition; and (B) Reporter response to canonical HIF PHD inhibitors: ciclopirox, DFO, DMOG, and DHB.

For convenience, before further description of the present invention, certain terms employed in the specification, examples, and appended claims are described here. These definitions should be read in light of the entire disclosure and as would be understood by a person skilled in the art.

The terms "a" and "an" are used herein to refer to one or to more than one (i.e., to at least one) of the grammatical object of the article. By way of example, "an element" can mean one or more elements, unless otherwise specified.

The term "isolated nucleic acid" refers to a polynucleotide of genomic, cDNA, or synthetic origin or some combination there of, which (1) is not associated with the cell in which the "isolated nucleic acid" is found in nature, or (2) is operably linked to a polynucleotide to which it is not linked in nature.

The term "operably linked", when describing the relationship between two nucleic acid regions, refers to a juxtaposition wherein the regions are in a relationship permitting them to function in their intended manner. For example, a control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

The term "vector" refers to an isolated nucleic acid capable of transporting another isolated nucleic acid to which it has been linked. One type of vector which may be used in accord with the invention is an episome, i.e., a nucleic acid capable of extrachromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules which, in their vector form are not bound to the chromosome.

The term "reporter" or "cell based reporter" refers to a recombinant DNA vector construct that is introduced into a cell in order to create a measurable signal of the occurrence of a cellular event. Such recombinant DNA is translated into protein, and such protein has the potential to generate a signal that can be measured by means known in the art, including but not limited to luminescent detection or fluorescent detection.

The term "polypeptide", and the terms "protein" and "peptide", which are used interchangeably herein, refer to a polymer of amino acids. Exemplary polypeptides include gene products, naturally-occurring proteins, homologs, orthologs, paralogs, fragments, and other equivalents, variants, and analogs of the foregoing.

A "post-translational" modification is a chemical alteration of a protein, caused by the same or by a different enzyme, after the protein being modified has been synthesized to completion. Post-translational modifications may modify protein function, or half life, and include prolyl-hydroxylation, ubiquitination, phosphorylation, prolyl isomerization and acylation.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

The term "high throughput screening" (HTS) refers to an automated, large-scale method to test small molecule inhibitors for inhibition of a particular enzyme activity or cellular process. HTS typically tests a library of different compounds to determined their activities.

The terms "small molecule inhibitor" and "inhibitor" are used interchangeably throughout this application and refer to a chemical entity that inhibits or prevents an enzyme's activity, wherein the activity of an enzyme is typically the enzyme's ability to convert a substrate into a product.

A "hit" refers to a compound identified to be an enzyme inhibitor in a high throughput screening assay.

The term "hypoxia" refers to decrease of oxygen supply to a cell or group of cells constituting a tissue or organ.

The term "hypoxic adaptation" refers to the transcriptional and translational response of a cell to hypoxia.

A "fusion protein" or "fusion polypeptide" refers to a chimeric protein as that term is known in the art. A fusion protein or polypeptide may be synthesized by methods known in the art. In many examples of fusion proteins, there are two different polypeptide sequences, and in certain cases, there may be more. The sequences may be linked in frame. A fusion protein may include a domain found (albeit in a different protein) in an organism that also expresses the first protein, or it may be an "interspecies", "intergenic", or related fusion expressed by different kinds of organisms. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. The fusion polypeptides may be fused to the N-terminus, the C-terminus, or the N- and C-terminus of the first polypeptide. Exemplary fusion proteins include polypeptides comprising a green fluorescent protein tag (GFP-tag), glutathione S transferase tag (GST-tag), histidine tag (His-tag), an immunoglobulin domain or an immunoglobulin binding domain.

The term "motif" generally refers to an amino acid sequence within a protein that has a particular function in the enzymatic process. The function can involve, for example, binding of a substrate, binding of a cofactor, or participation in catalysis.

"Target genes" of a transcription factor are native cellular genomic sequences whose transcriptional expression is controlled by the transcription factor.

A "transcription factor" is a protein that, through binding to a cellular genomic DNA sequence or by facilitating the interaction of other proteins to such sequence, allows synthesis of mRNA, "transcription", from such genomic DNA sequence.

The term "erythropoiesis" refers to the cellular process of new red blood cell generation.

The term "ischemic diseases" refers to cellular, tissue, or organ damage resulting from a hypoxic episode that causes tissue organ dysfunction.

The term "transplantation" refers to the transfer of a tissue or organ from one body or body part to another.

The terms "hydrocarbon group" and "hydrocarbon linker", as used herein, are, in a first embodiment, composed solely of carbon and hydrogen. In different embodiments, one or more of the hydrocarbon groups or linkers can contain precisely, or a minimum of, or a maximum of, for example, one, two, three, four, five, six, seven, eight, nine, ten, eleven, twelve, thirteen, fourteen, fifteen, sixteen, seventeen, eighteen, nineteen, or twenty carbon atoms, or a number of carbon atoms within a particular range bounded by any two of the foregoing carbon numbers. Hydrocarbon groups or linkers in different compounds described herein, or in different positions of a compound, may possess the same or different number (or preferred range thereof) of carbon atoms in order to independently adjust or optimize the activity or other characteristics of the compound.

The hydrocarbon groups or linkers can be, for example, saturated and straight-chained (i.e., straight-chained alkyl groups or alkylene linkers). Some examples of straight-chained alkyl groups (or alkylene linkers) include methyl (or methylene linker, i.e., —$CH_2$—, or methine linker), ethyl (or ethylene or dimethylene linker, i.e., —$CH_2CH_2$-linker), n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, and n-eicosyl groups (or their respective linker analogs).

The hydrocarbon groups or linkers can alternatively be saturated and branched (i.e., branched alkyl groups or alkylene linkers). Some examples of branched alkyl groups include isopropyl, isobutyl, sec-butyl, t-butyl, isopentyl, neopentyl, 2-methylpentyl, 3-methylpentyl, and the numerous $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ saturated and branched hydrocarbon groups. Some examples of branched alkylene linkers are those derived by removal of a hydrogen atom from one of the foregoing exemplary branched alkyl groups (e.g., isopropylene, —$CH(CH_3)CH_2$—).

The hydrocarbon groups or linkers can alternatively be saturated and cyclic (i.e., cycloalkyl groups or cycloalkylene linkers). Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane). Some examples of cycloalkylene linkers are those derived by removal of a hydrogen atom from one of the foregoing exemplary cycloalkyl groups.

The hydrocarbon groups or linkers can alternatively be unsaturated and straight-chained (i.e., straight-chained olefinic or alkenyl groups or linkers). The unsaturation occurs by the presence of one or more carbon-carbon double bonds and/or one or more carbon-carbon triple bonds. Some examples of straight-chained olefinic groups include vinyl, propen-1-yl (allyl), 3-buten-1-yl ($CH_2$=CH—$CH_2$—$CH_2$—), 2-buten-1-yl ($CH_2$—CH=CH—$CH_2$—), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl (2-propynyl), and the numerous $C_7$, $C_8$, $C_9$, $C_{10}$, $C_{11}$, $C_{12}$, and higher unsaturated and straight-chained hydrocarbon groups. Some examples of straight-chained olefinic linkers are those derived by removal of a hydrogen atom from one of the foregoing exemplary straight-chained olefinic groups (e.g., vinylene, —CH=CH—, or vinylidene).

The hydrocarbon groups or linkers can alternatively be unsaturated and branched (i.e., branched olefinic or alkenyl groups or linkers). Some examples of branched olefinic groups include propen-2-yl, 3-buten-2-yl ($CH_2$=CH—CH.—$CH_3$), 3-buten-3-yl ($CH_2$=C.—$CH_2$—$CH_3$), 4-penten-2-yl, 4-penten-3-yl, 3-penten-2-yl, 3-penten-3-yl, 2,4-pentadien-3-yl, and the numerous $C_6$, $C_7$, $C_8$, $C_9$, $C_{10}$, $C_{11}$, $C_{12}$, and higher unsaturated and branched hydrocarbon groups. Some examples of branched olefinic linkers are those derived by removal of a hydrogen atom from one of the foregoing exemplary branched olefinic groups.

The hydrocarbon groups or linkers can alternatively be unsaturated and cyclic (i.e., cycloalkenyl groups or cycloalkenylene linkers). The unsaturated and cylic group can be aromatic or aliphatic. Some examples of unsaturated and cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group can also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene. Some examples of cycloalkenylene linkers are those derived by removal of a hydrogen atom from one of the foregoing exemplary cycloalkenyl groups (e.g., phenylene and biphenylene).

One or more of the hydrocarbon groups or linkers may also include one or more heteroatoms (i.e., non-carbon and non-hydrogen atoms), such as one or more heteroatoms selected from oxygen, nitrogen, sulfur, and halide atoms, as well as groups containing one or more of these heteroatoms (i.e., heteroatom-containing groups). Some examples of oxygen-containing groups include hydroxy (OH), carbonyl-containing (e.g., carboxylic acid, ketone, aldehyde, carboxylic ester, amide, and urea functionalities), nitro ($NO_2$), carbon-oxygen-carbon (ether), sulfonyl, and sulfonyl (i.e., sulfoxide), and amine oxide groups. The ether group can also be a polyalkyleneoxide group, such as a polyethyleneoxide group. Some examples of nitrogen-containing groups include primary amine, secondary amine, tertiary amine, quaternary amine, cyanide (i.e., nitrile), amide (i.e., —C(O)$NR_2$ or —NRC(O), wherein R is independently selected from hydrogen atom and hydrocarbon group, as described above), nitro, urea, imino, and carbamate, wherein it is understood that a quaternary amine group necessarily possesses a positive charge and requires a counteranion. Some examples of sulfur-containing groups include mercapto (i.e., —SH), thioether (i.e., sulfide), disulfide, sulfoxide, sulfone, sulfonate, and sulfate groups. Some examples of halide atoms considered herein include fluorine, chlorine, and bromine. One or more of the heteroatoms described above (e.g., oxygen, nitrogen, and/or sulfur atoms) can be inserted between carbon atoms (e.g., as —O—, —NR—, or —S—) in any of the hydrocarbon groups described above to form a heteroatom-substituted hydrocarbon group or linker. Alternatively, or in addition, one or more of the heteroatom-containing groups can replace one or more hydrogen atoms on the hydrocarbon group or linker.

In particular embodiments, the hydrocarbon group is, or includes, a cyclic group. The cyclic hydrocarbon group may be, for example, monocyclic by containing a single ring without connection or fusion to another ring. The cyclic hydrocarbon group may alternatively be, for example, bicyclic, tricyclic, tetracyclic, or a higher polycyclic ring system by having at least two rings interconnected and/or fused.

In some embodiments, the cyclic hydrocarbon group is carbocyclic, i.e., does not contain ring heteroatoms (i.e., only ring carbon atoms). In different embodiments, ring carbon atoms in the carbocylic group are all saturated, or a portion of the ring carbon atoms are unsaturated, or the ring carbon atoms are all unsaturated (as found in aromatic carbocyclic groups, which may be monocyclic, bicyclic, tricylic, or higher polycyclic aromatic groups).

In some embodiments, the hydrocarbon group is, or includes, a cyclic or polycyclic group that includes at least one ring heteroatom (for example, one, two, three, four, or higher number of heteroatoms). Such ring heteroatom-substituted cyclic groups are referred to herein as "heterocyclic groups". As used herein, a "ring heteroatom" is an atom other than carbon and hydrogen (typically, selected from nitrogen, oxygen, and sulfur) that is inserted into, or replaces a ring carbon atom in, a hydrocarbon ring structure. In some embodiments, the heterocyclic group is saturated, while in other embodiments, the heterocyclic group is unsaturated (i.e., aliphatic or aromatic heterocyclic groups, wherein the aromatic heterocyclic group is also referred to herein as a "heteroaromatic ring", or a "heteroaromatic fused-ring system" in the case of at least two fused rings, at least one of which contains at least one ring heteroatom). In some embodiments, the heterocyclic group is bound via one of its ring carbon atoms to another group (i.e., other than hydrogen atom and adjacent ring atoms), while the one or more ring heteroatoms are not bound to another group. In other embodiments, the heterocyclic group is bound via one of its heteroatoms to another group, while ring carbon atoms may or may not be bound to another group.

Some examples of saturated heterocyclic groups include those containing at least one oxygen atom (e.g., oxetane, tetrahydrofuran, tetrahydropyran, 1,4-dioxane, 1,3-dioxane, and 1,3-dioxepane rings), those containing at least one nitrogen atom (e.g., pyrrolidine, piperidine, piperazine, imidazolidine, azepane, and decahydroquinoline rings), those containing at least one sulfur atom (e.g., tetrahydrothiophene, tetrahydrothiopyran, 1,4-dithiane, 1,3-dithiane, and 1,3-dithiolane rings), those containing at least one oxygen atom and at least one nitrogen atom (e.g., morpholine and oxazolidine rings), those containing at least one oxygen atom and at least one sulfur atom (e.g., 1,4-thioxane), and those containing at least one nitrogen atom and at least one sulfur atom (e.g., thiazolidine and thiamorpholine rings).

Some examples of unsaturated heterocyclic groups include those containing at least one oxygen atom (e.g., furan, pyran, 1,4-dioxin, and dibenzodioxin rings), those containing at least one nitrogen atom (e.g., pyrrole, imidazole, pyrazole, pyridine, pyrazine, pyrimidine, 1,3,5-triazine, azepine, diazepine, indole, purine, benzimidazole, indazole, 2,2'-bipyridine, quinoline, isoquinoline, phenanthroline, 1,4,5,6-tetrahydropyrimidine, 1,2,3,6-tetrahydropyridine, 1,2,3,4-tetrahydroquinoline, quinoxaline, quinazoline, pyridazine, cinnoline, 5,6,7,8-tetrahydroquinoxaline, 1,8-naphthyridine, and 4-azabenzimidazole rings), those containing at least one sulfur atom (e.g., thiophene, thianaphthene, and benzothiophene rings), those containing at least one oxygen atom and at least one nitrogen atom (e.g., oxazole, isoxazole, benzoxazole, benzisoxazole, oxazoline, 1,2,5-oxadiazole (furazan), and 1,3,4-oxadiazole rings), and those containing at least one nitrogen atom and at least one sulfur atom (e.g., thiazole, isothiazole, benzothiazole, benzoisothiazole, thiazoline, and 1,3,4-thiadiazole rings).

In one aspect, the invention is directed to HIF PHD-inhibiting compounds having chemical structures encompassed by the following generic structure:

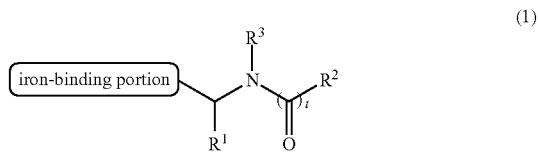

(1)

In Formula (1), the iron-binding portion has a chemical structure that includes at least one iron-binding functional group, such as, for example, carboxylic acid, carboxylic acid ester, keto, amino, amido, imino, ureido, nitro, hydroxy, nitrile, and amine oxide groups. The iron-binding functional groups reside on a hydrocarbon skeleton. The hydrocarbon skeleton corresponds to any of the hydrocarbon groups described above. Thus, the iron-binding portion corresponds to any of the hydrocarbon groups described above (i.e., hydrocarbon skeleton) that have been modified to contain one or more heteroatoms and/or heteroatom groups, particularly those iron-binding functional groups described above.

The iron-binding portion preferably contains at least three and up to twenty carbon atoms. The number of carbon atoms in the iron-binding portion includes all carbon atoms, including those contained in heteroatom groups, such as the carbon atom in a carbonyl group or in secondary or tertiary amino groups. In different embodiments, the iron-binding portion contains three, four, five, six, seven, eight, nine, ten, eleven, twelve, thirteen, fourteen, fifteen, sixteen, seventeen, eighteen, nineteen, or twenty carbon atoms, or a number of carbon atoms within a range bounded by any of the foregoing number of carbon atoms.

In some embodiments, the iron-binding portion includes a monocyclic, bicyclic, tricyclic, or higher polycyclic group. The cyclic, bicyclic, tricyclic, or higher polycyclic group can be carbocylic or heterocyclic. In particular embodiments, the iron-binding portion includes an aromatic or heteroaromatic monocyclic, bicyclic, tricyclic, or higher polycyclic group. In some embodiments, the cyclic, bicyclic, tricyclic, or higher polycyclic group in the iron-binding portion includes at least one, two, or three polar groups, particularly small polar groups (as further described below), on any position of the ring system, and particularly on portions of the ring or ring system more remote or farthest from the branched portion. In other embodiments, the cyclic, bicyclic, tricyclic, or higher polycyclic group in the iron-binding portion is directly bound to the branched portion, while in other embodiments, a linker of up to one, two, three, or four atom lengths connects the ring or ring system with the branched portion.

Subscript t in formula (1) is a number of 0 or 1. When t is 0, the subtended carbonyl group is not present, thereby resulting in an amino group in the branched portion (the shown N atom is then directly bound to $R^2$). When t is 1, the subtended carbonyl group is present, thereby resulting in an amido group in the branched portion.

As shown in formula (1), the iron-binding portion is attached to an amino- or amido-containing branched portion, also referred to herein as "the branched portion". In the branched portion, $R^1$ is a monocyclic group, such as any of the saturated or unsaturated, and carbocyclic or heterocyclic monocyclic groups described above. In some embodiments, the monocyclic group of $R^1$ contains ring hydrogen atoms that are all unsubstituted (i.e., ring hydrogen atoms not replaced with a substituting group). The ring hydrogen atoms refer to hydrogen atoms on ring carbon atoms as well as on ring heteroatoms. Such a monocyclic group is herein referred to as an unsubstituted monocyclic group (although the monocyclic group may contain ring-heteroatom substitution). In other embodiments, the monocyclic group of $R^1$ is substituted by having at least ring hydrogen atom that has been substituted with a substituting (i.e., non-hydrogen atom) group. The at least one substituting group on $R^1$ can be selected from, for example, a group —$R^4$ (as further described below), or a polar group, particularly small polar groups containing up to three, four, five, six, seven, eight, nine, ten, eleven, or twelve non-hydrogen atoms, such as —$C(O)R^4$, —$NR^4_2$, —$NO_2$, —$C(O)NR^4_2$, —$NR^4C(O)R^4$, —$C(O)OR^4$, —$NR^4C(O)NR^4_2$, —$NR^4C(O)OR^4$, —$SO_2R^4$, nitrile, and halogen atom, wherein $R^4$ is, independently, a hydrogen atom or a non-cyclic hydrocarbon group, preferably containing up to one, two, three, four, five, six, seven, eight, or nine carbon atoms (e.g., methyl, ethyl, n-propyl, or isopropyl). Where $R^4$ is repeated in a group (e.g., —$NR^4_2$), $R^4$ can be the same or different (i.e., $R^4$ is independently selected within the same group and between different groups). In some embodiments, $R^4$ is a saturated non-cyclic hydrocarbon group, an unsaturated non-cyclic hydrocarbon group, a saturated non-cyclic heteroatom-containing hydrocarbon group, an unsaturated non-cyclic heteroatom-containing group, or a branched or straight-chained alkyl group. In particular embodiments, $R^4$ is selected from one or more hydrocarbon groups having at least one and up to two, three, or four carbon atoms (e.g., methyl, ethyl, vinyl, allyl, n-propyl, isopropyl, n-butyl, isobutyl, sec-butyl, and t-butyl groups).

In some embodiments, $R^1$ is a carbocyclic group, i.e., carbocyclic monocyclic or bicyclic group, which may be saturated, aliphatic, or aromatic. The carbocyclic groups particularly considered herein have up to six, seven, eight, nine, or ten carbon atoms (including ring and non-ring carbon atoms). Some particular examples of such groups include phenyl, tolyl, biphenyl, diphenylmethinyl (i.e., $Ph_2CH$—, where Ph=phenyl), naphthyl, cyclohexyl, and dicyclohexyl groups. In further embodiments, the carbocyclic group is substituted with at least one polar group, particularly a small polar group, as described above. In more particular embodiments, the polar group is selected from hydroxy, carboxy, methoxy, ethoxy, propoxy, isopropoxy, halogen atom, —$NH_2$, nitro, and ammonium groups. A particular example of such a group substituted carbocyclic group is a phenyl group substituted in the o-, m-, or p-position (relative to the bond of $R^1$ with the rest of the branching portion) with a polar group. In particular embodiments, $R^1$ is, or includes, a phenyl group containing two polar groups, particularly where the polar groups are selected from hydroxy and/or alkoxy groups. The two polar groups (and particularly, two alkoxy and/or hydroxy groups) can be located on o-positions, on m-positions, on o- and m-positions, on o- and p-positions, or on m- and p-positions. In other embodiments, $R^1$ is, or includes, a phenyl group containing three or four polar groups, particularly where the polar groups are selected from hydroxy and/or alkoxy groups. In particular embodiments, the alkoxy groups on the phenyl ring are selected from methoxy, ethoxy, n-propoxy, and isopropoxy. In other embodiments, $R^1$ is a monocyclic or bicyclic heteroaromatic group, such as any of these groups described above. The monocyclic or bicyclic heteroaromatic group can be unsubstituted, or alternatively, substituted with one or more polar groups.

In some embodiments, the monocyclic group of $R^1$ is directly attached to the shown carbon atom of the branched portion (i.e., as shown in Formula 1). In other embodiments, the monocyclic group of $R^1$ is substituted with one or more linkers that link the monocyclic group with the shown carbon atom. The linker is generally no more than six atom lengths (in particular embodiments, no more than five, four, three, two, or one atom length). The linker can be, for example, —$R^4$—, —$C(O)$—, —$C(O)R^4$—, —$NR^4$—, —$C=NR^4$—, —$N=NR^4$—, —$C=NR^4$—, —$C=N$—$NR^4$—, —$O$—, —$S$—, —$C(O)NR^4$—, —$NR^4C(O)R^4$—, —$C(O)O$—, —$C(O)OR^4$—, —$NR^4C(O)NR^4$—, —$NR^4C(O)OR^4$—, $NR^4C(O)OR^4$—, —$SO_2R^4$—, or a combination thereof. Some examples of —R$^4$— linkers include methylene (—CH$_2$—), ethylene (—CH$_2$CH$_2$—), and vinylene (—CH=CH—). Some examples of —C(O)R$^4$— linkers include —C(O)CH$_2$— and —C(O)CH$_2$CH$_2$—. Some examples of —NR$^4$— linkers include —NH—, —N(CH$_3$)—, —N(CH$_2$CH$_3$)—, —N(iPr)-, —N(cyclopentyl)-, and —N(phenyl)-. Some examples of —C=NR$^4$— linkers include —C=N—CH$_2$—, —C=N—CH$_2$CH$_2$—, and —C=N—CH=CH—.

R$^2$ in formula (1) can be any of the monocyclic groups described above for R$^1$. R$^1$ can also be selected from —R$^5$, —C(O)R$^5$, —NR$^5$$_2$, —OR$^5$, —NO$_2$, —C(O)NR$^5$$_2$, —NR$^5$C(O)R$^5$, —C(O)OR$^5$, —NR$^5$C(O)NR$^5$$_2$, —NR$^5$C(O)OR$^5$, —SO$_2$R$^5$, nitrile, and halogen atom, wherein R$^5$ is, independently, any of the cyclic, polycyclic, or non-cyclic (i.e., straight-chained or branched), saturated or unsaturated, substituted or unsubstituted hydrocarbon groups, described above, containing up to nine carbon atoms. In particular embodiments, R$^5$ contains up to one, two, three, four, five, six, seven, eight, or nine carbon atoms. Generally, when t is 1 (i.e., subtended carbonyl is present), R$^2$ is not —C(O)R$^5$, —C(O)NR$^5$$_2$, —C(O)OR$^5$, or a halogen atom. When R$^2$ is a monocytic, bicyclic, tricyclic, or higher polycyclic group, the cyclic group may or may not also include one or more ring-heteroatoms selected from nitrogen, oxygen, and sulfur and/or one or more ring functional groups selected from —C(O)— and —C(S)—. The cyclic hydrocarbon group of R$^5$ may or may not also be substituted with one or more groups selected from —R$^4$, —C(O)R$^4$, —NR$^4$$_2$, —OR$^4$, —NO$_2$, —C(O)NR$^4$$_2$, —NR$^4$C(O)R$^4$, —C(O)OR$^4$, —NR$^4$C(O)NR$^4$$_2$, —R$^4$C(O)OR$^4$, —SO$_2$R$^4$, nitrile, and halogen atom, as described above.

In particular embodiments, R$^2$ includes a straight-chained or branched hydrocarbon group containing up to one, two, three, four, five, or six carbon atoms, which may or may not also include a carbocyclic or heterocyclic ring or ring system. In further embodiments, R$^2$ includes a straight-chained or branched hydrocarbon group containing up to one, two, three, four, five, or six carbon atoms, which also includes a carbocyclic or heterocyclic ring or ring system, such as a phenyl ring. For example, R$^2$ may be —CH$_2$-phenyl, —CR$^4$$_2$-phenyl, —CH$_2$CH$_2$-phenyl, —CH$_2$CR$^4$$_2$-phenyl, or —CH=CH— phenyl, wherein R$^4$ in the latter examples is generally an alkyl group containing one, two, or three carbon atoms.

In other particular embodiments, R$^2$ is, or includes, a monocyclic, bicyclic, or higher polycyclic aromatic or heteroaromatic group, such as any of these groups described above. The aromatic or heteroaromatic group can be substituted, or alternatively, substituted with one or more polar or non-polar groups. In more particular embodiments, R$^2$ is, or includes, a heteroaromatic group that includes at least one (e.g., one, two, three, or four) ring nitrogen atoms. In further particular embodiments, R$^2$ is, or includes, a monocyclic heteroaromatic group that includes at least one ring nitrogen atom, such as a 2-, 3-, or 4-pyridyl group, or a pyrrolyl, pyrazinyl, imidazolyl, or triazinyl group. In some embodiments, the aromatic or heteroaromatic group of R$^2$ is directly bound to the shown carbonyl group (when t is 1) or the shown nitrogen atom (when t is 0). In other embodiments, the aromatic or heteroaromatic group of R$^2$ is indirectly bound, via a linker (such as any of the linkers described above, as for R$^1$), to the shown carbonyl group (when t is 1) or the shown nitrogen atom (when t is 0). When t is 0, and R$^2$ is, or includes, a heteroaromatic group, the heteroaromatic group generally binds to the shown nitrogen atom by a carbon atom, located either on the heteroaromatic group or on a linker connecting the heteroaromatic group with the shown nitrogen atom.

R$^3$ in formula (1) can be a hydrogen atom or a hydrocarbon group containing up to six carbon atoms. In different embodiments, the hydrocarbon group of R$^3$ contains up to five, four, three, two, or one carbon atom.

In some embodiments, R$^2$ and R$^3$ are not interconnected. In other embodiments, R$^2$ and R$^3$ are interconnected to form in a cyclic structure. When t is 0, the cyclic structure is a cyclic amine. When t is 1, the cyclic structure is a cyclic amide. R$^2$ and R$^3$ can form an interconnected structure by replacing a hydrogen atom from each of R$^2$ and R$^3$ with a bond connecting R$^2$ and R$^3$. A double bond can also be included in said cyclic structure by replacing four hydrogen atoms from R$^2$ and R$^3$ with a double bond connecting R$^2$ and R$^3$. In particular embodiments, the group —NR$^2$R$^3$ (i.e., when t is 0), forms a cyclic amine containing up to six ring carbon atoms. When R$^2$ and R$^3$ are hydrocarbon groups without heteroatoms, the resulting cyclic amine contains only one nitrogen ring atom as a heteroatom. Some examples of such cyclic amine groups when R$^2$ and R$^3$ are interconnected include pyrrolidinyl, piperidinyl, azepanyl, and unsaturated forms thereof (e.g., pyridinyl and pyrrolyl). When R$^2$ and R$^3$ are hydrocarbon groups with one or more heteroatoms, the resulting cyclic amine includes the shown nitrogen atom as a ring heteroatom, along with one or more ring heteroatoms provided by R$^2$ and R$^3$. Thus, when R$^2$ and R$^3$ are interconnected, —NR$^2$R$^3$ can represent, for example, an imidazolyl, pyrazolyl, piperazinyl, pyrazinyl, pyrimidinyl, triazinyl, oxazolyl, morpholinyl, indolyl, thiazolyl, quinolinyl, isoquinolyl, or other such groups containing two or three ring nitrogen atoms, or one or two ring nitrogen atoms along with one or two other heteroatoms. The resulting interconnection result in a monocyclic, bicyclic, tricycli, or higher polycyclic ring or ring system. Cyclic structures that contain an amide group can result in an analogous manner if R$^2$ and R$^3$ are interconnected when t is 1.

In a first set of embodiments, the iron-binding portion has the following substituted-quinolinyl structural formula:

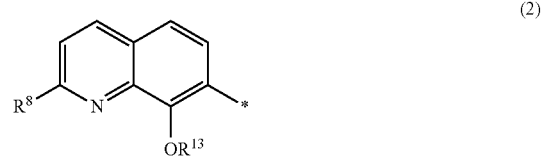

(2)

In Formula (2), R$^8$ can be a hydrogen atom, or a hydrocarbon group containing up to three carbon atoms, or a polar group, particularly a small polar group, and more particularly, a small polar group selected from —C(O)OH, —OH, halogen atom, and nitro group, as well as methylene-linked versions thereof (e.g., —CH$_2$—COOH or —CH$_2$—OH). Preferably, R$^8$ is a polar group. R$^{13}$ is selected from hydrogen atom and alkyl group containing up to three carbon atoms. In some embodiments, any one, two, or three of the ring hydrogen atoms shown in Formula (2) can be replaced with polar groups, particularly on the 2-, 3-, 4-, and/or 5-position (preferably, in addition to R$^8$ at the 2-position already being a polar group). The asterisk shown in Formula (2) indicates the bond in the iron-binding portion connected with the branched portion (i.e., to the carbon in the branched portion bearing the R$^1$ substituent). Although the bond depicted in Formula (2) connected with the branched portion is depicted on the 7-position of the shown quinoline structure, in some embodiments, the connecting bond is instead located at the 6-position of the shown quinoline structure. This concept is extended to any of the quinolinyl structures described in this application.

In particular embodiments of Formula (2), t in the branching portion is 0, thereby resulting in compounds encompassed by the following chemical structure:

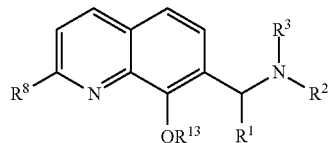

(2a)

In other particular embodiments of Formula (2), t in the branching portion is 1, thereby resulting in compounds encompassed by the following chemical structure:

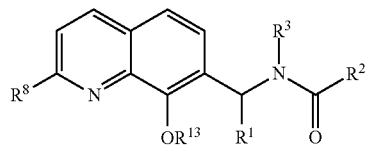

(2b)

In some embodiments, $R^{13}$ in Formula (2) is not interconnected with $R^1$ or $R^3$. In other embodiments, $R^{13}$ is interconnected with $R^3$ to form a cyclic oxazole group. In a particular embodiment where $R^{13}$ is H and $R^3$ is methyl, the H and hydrogen atom from methyl can be substituted with a bond connecting $R^{13}$ and $R^3$, the result of which is shown by the following formula:

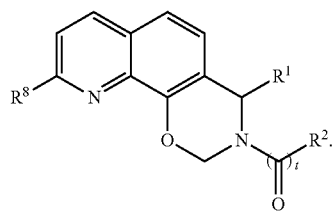

(2c)

In a second set of embodiments, the iron-binding portion has the following substituted-quinolinyl structural formula:

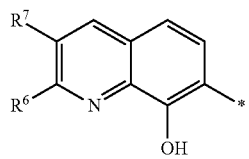

(3)

In Formula (3), $R^6$ and $R^7$ are independently selected from hydrogen atom, hydrocarbon group containing up to three carbon atoms, and polar groups, particularly small polar groups, such as those selected from —C(O)OH, —OH, and nitro group, as well as methylene-linked versions thereof. In particular embodiments, at least one of $R^6$ and $R^7$ (preferably, at least $R^6$, or only $R^6$) is a polar group or methylene-linked version thereof. In some embodiments, any one, two, or three of the ring hydrogen atoms shown in Formula (3) can be replaced with polar groups, particularly on the 2-, 3-, 4-, and/or 5-position (preferably, in addition to $R^6$ at the 2-position already being a polar group). In some embodiments, the 8-OH group shown in Formula (3) can be interconnected with $R^3$ by having the shown hydrogen atom absent and the shown oxygen atom instead linked with $R^3$ to form a cyclic structure, analogous to that shown in Formula (2c).

In a third set of embodiments, the iron-binding portion has the following α-ketoglutarate mimicking structure:

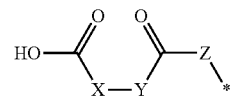

(4)

In Formula (4), X and Y are independently selected from —CHR$^{15}$— and —NR$^{16}$—, wherein $R^{15}$ and $R^{16}$ are independently selected from hydrogen atom and hydrocarbon groups containing one to four carbon atoms. In some embodiments, X and Y are selected from —CH$_2$— and —NH— groups. In some embodiments, both X and Y are —CHR$^{15}$— groups. In other embodiments, one of X and Y is a —CHR$^{15}$— while another of X and Y is a —NR$^{16}$— group. Generally, X and Y are not both —NR$^{16}$— groups. In some embodiments, both $R^{15}$ and $R^{16}$ are hydrogen atoms. In other embodiments, one of $R^{15}$ and $R^{16}$ is a hydrogen atom while another of $R^{15}$ and $R^{16}$ is a hydrocarbon group. In other embodiments, both of $R^{15}$ and $R^{16}$ are hydrocarbon groups. In some embodiments, $R^{15}$ and $R^{16}$ are not interconnected, while in other embodiments, $R^{15}$ and $R^{16}$ are interconnected to form a ring. Z is a carbonyl (i.e., —C(O)—) or carbonyl-mimicking group. The carbonyl-mimicking group is any group that provides a double bond oxo group as found in a carbonyl group. Some examples of carbonyl-mimicking groups include sulfinyl, sulfonyl, amine oxide (e.g., oxime), phosphine oxide, and phosphinate groups. The connecting carbon (indicated by asterisk) in Formula (4) may be linked to the branched portion either directly or via a linker, typically up to three or four atom lengths, such as a methylene or ethylene linker.

In particular embodiments of the third set of embodiments, the iron-binding portion has the following α-ketoglutarate mimicking structure:

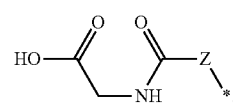

(4a)

In other particular embodiments of the third set of embodiments, the iron-binding portion has the following α-ketoglutarate mimicking structure:

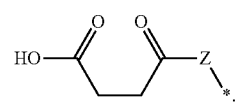

(4b)

In other particular embodiments of the third set of embodiments, the iron-binding portion has the following α-ketoglutarate mimicking structure:

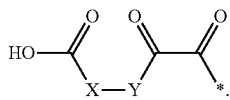

(4c)

In particular embodiments of Formula (4c), X is —CH₂— and Y is —NH—, or vice-versa. In other embodiments of Formula (4c), X and Y are both —CH₂—.

In other particular embodiments of the third set of embodiments, the iron-binding portion has the following α-ketoglutarate mimicking structure:

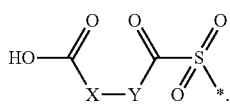

(4d)

In particular embodiments of Formula (4d), X is —CH₂— and Y is —NH—, or vice-versa. In other embodiments of Formula (4d), X and Y are both —CH₂—.

In a fourth set of embodiments, the iron-binding portion has the following structural formula:

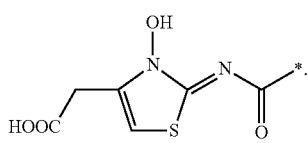

(5)

In a fifth set of embodiments, the iron-binding portion has the following structural formula:

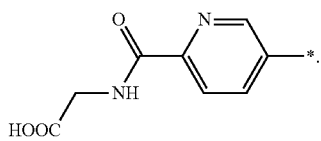

(6)

In a sixth set of embodiments, the iron-binding portion has the following structural formula:

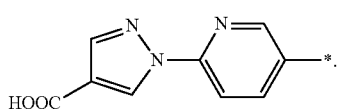

(7)

In a seventh set of embodiments, the iron-binding portion has the following structural formula:

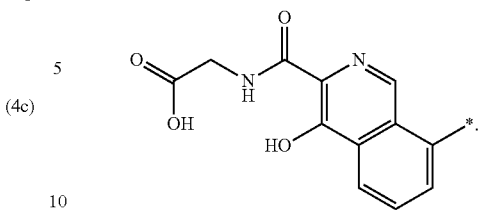

(8)

In an eighth set of embodiments, the iron-binding portion has the following structural formula:

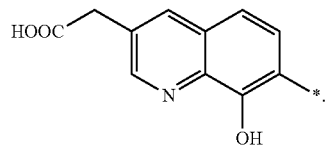

(9)

In a ninth set of embodiments, the iron-binding portion has the following structural formula:

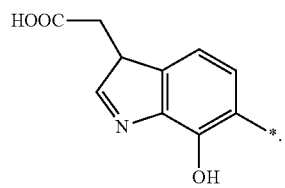

(10)

In a tenth set of embodiments, the iron-binding portion has the following structural formula:

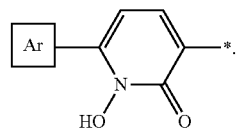

(11)

In Formula (11), Ar represents an aromatic or heteroaromatic ring that may or may not be substituted with one or more polar or non-polar groups, as described above. The aromatic or heteroaromatic ring can be monocyclic, bicyclic, or tricyclic. Typically, Ar is bound directly (i.e., without a linker), although linkers of one or two atom lengths (e.g., methylene or ethylene) may be included in some embodiments. In particular embodiments, Ar is, or includes, a phenyl ring. In other particular embodiments, Ar is a monocyclic heteroaromatic ring, and more particularly, a monocyclic heteroaromatic ring containing at least one oxygen, nitrogen, or sulfur atom, and more particularly, wherein at least one heteroatom and/or polar group is directed away (more typically, farthest away) from the structure to which the Ar group is attached.

In a particular embodiment of the tenth embodiment, the iron-binding portion has the following structural formula:

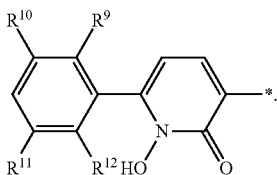
(11a)

In Formula (11a), $R^9$, $R^{10}$, $R^{11}$, and $R^{12}$ are independently selected from hydrogen atom, halogen atom, and hydroxy group. In some embodiments, $R^9$, $R^{10}$, $R^{11}$, and $R^{12}$ are all hydrogen atoms. In other embodiments, at least one or two of $R^9$, $R^{10}$, $R^{11}$, and $R^{12}$ (and more particularly, at least one or two of $R^{10}$ and $R^{11}$) are selected from halogen atom. In other embodiments, at least one or two of $R^9$, $R^{10}$, $R^{11}$, and $R^{12}$ (and more particularly, at least one or two of $R^{10}$ and $R^{11}$) are selected from hydroxy group. In yet other embodiments, at least one of $R^9$, $R^{10}$), $R^{11}$, and $R^{12}$ is a halogen atom and at least one is a hydroxy group. In still other embodiments, three or four of $R^9$, $R^{10}$, $R^{11}$, and $R^{12}$ are selected from halogen atom and hydroxy group.

In another particular embodiment of the tenth embodiment, the iron-binding portion has the following structural formula:

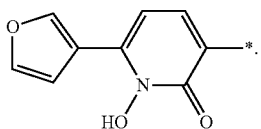
(11b)

In an eleventh set of embodiments, the iron-binding portion has the following structural formula:

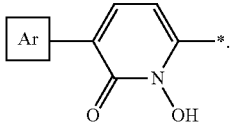
(12)

In Formula (12), Ar represents an aromatic or heteroaromatic ring that may or may not be substituted with one or more polar or non-polar groups, as described above. The scope and exemplary embodiments covered by Ar is provided under Formula (11) above, incorporated by reference herein.

In a particular embodiment of the eleventh embodiment, the iron-binding portion has the following structural formula:

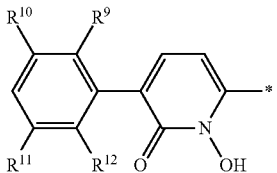
(12a)

In Formula (12a), $R^9$, $R^{10}$, $R^{11}$, and $R^{12}$ are independently selected from hydrogen atom, halogen atom, and hydroxy group. The scope and exemplary embodiments provided under Formula (11a) for $R^9$, $R^{10}$, $R^{11}$, and $R^{12}$ is incorporated by reference herein.

In another particular embodiment of the eleventh embodiment, the iron-binding portion has the following structural formula:

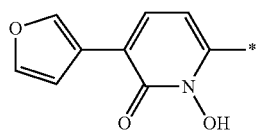
(12b)

In particular embodiments of Formulas (11a) and (12a), $R^9$, $R^{10}$, $R^{11}$, and $R^{12}$ are all hydrogen atoms. In other particular embodiments, one, two, three, or all of $R^9$, $R^{10}$, $R^{11}$, and $R^{12}$ are selected from fluoro, chloro, and/or bromo atoms. In other particular embodiments, one, two, three, or four of $R^9$, $R^{10}$, $R^{11}$, and $R^{12}$ are hydroxy groups.

In a twelfth set of embodiments, the iron-binding portion has the following structural formula:

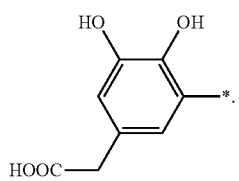
(13)

In a thirteenth set of embodiments, the iron-binding portion has the following structural formula:

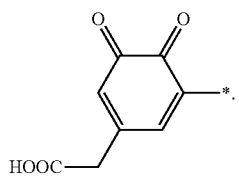
(14)

In a fourteenth set of embodiments, the iron-binding portion has the following structural formula:

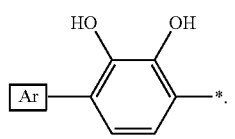
(15)

In formula (15), Ar represents an aromatic or heteroaromatic ring that may or may not be substituted with one or more polar or non-polar groups, as described above. The scope and exemplary embodiments covered by Ar is provided under Formula (11) above, incorporated by reference herein.

In a particular embodiment of the fourteenth embodiment, the iron-binding portion has the following structural formula:

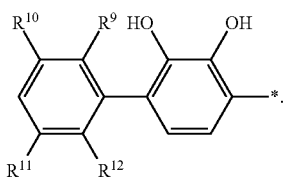

(15a)

In Formula (15a), $R^9$, $R^{10}$, $R^{11}$, and $R^{12}$ are independently selected from hydrogen atom, halogen atom, and hydroxy group. The scope and exemplary embodiments provided under Formulas (11a) and (12b) for $R^9$, $R^{10}$, $R^{11}$, and $R^{12}$ is incorporated by reference herein.

In another particular embodiment of the fourteenth embodiment, the iron-binding portion has the following structural formula:

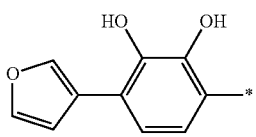

(15b)

In a fifteenth set of embodiments, the iron-binding portion has the following structural formula:

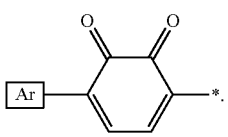

(16)

In Formula (16), Ar represents an aromatic or heteroaromatic ring that may or may not be substituted with one or more polar or non-polar groups, as described above. The scope and exemplary embodiments covered by Ar is provided under Formula (11) above, incorporated by reference herein.

In a particular embodiment of the fifteenth embodiment, the iron-binding portion has the following structural formula:

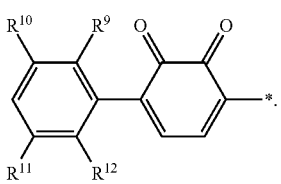

(16a)

In Formula (16a), $R^9$, $R^{10}$, $R^{11}$, and $R^{12}$ are independently selected from hydrogen atom, halogen atom, and hydroxy group. The scope and exemplary embodiments provided under Formulas (11a) and (12b) for $R^9$, $R^{10}$, $R^{11}$, and $R^{12}$ is incorporated by reference herein.

In another particular embodiment of the fifteenth embodiment, the iron-binding portion has the following structural formula:

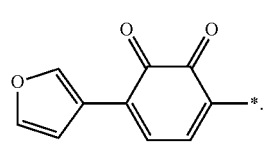

(16b)

In a sixteenth set of embodiments, the iron-binding portion has the following structural formula:

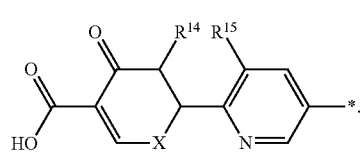

(17)

In Formula (17), $R^{14}$ and $R^{15}$ are selected from hydrogen atom, a hydrocarbon group containing up to three carbon atoms, or a polar group, such as a small polar group, as described above. X in Formula (17) is either —$CH_2$—, —O—, —S—, or —$NR^4$, wherein $R^4$ is as defined above (typically, —$NR^4$ is —NH—). In some embodiments, X is not —$CH_2$—. In some embodiments, $R^{14}$ and $R^{15}$ are not interconnected. In other embodiments, $R^{14}$ and $R^{15}$ are interconnected to form a ring, thereby forming a tricyclic structure in Formula (17).

In a particular embodiment of the sixteenth embodiment, $R^{14}$ and $R^{15}$ are interconnected to form a bridging aromatic ring, thus producing an iron-binding portion having the following structural formula:

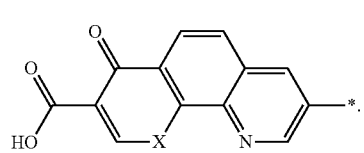

(17a)

In a seventeenth set of embodiments, the iron-binding portion has the following structural formula:

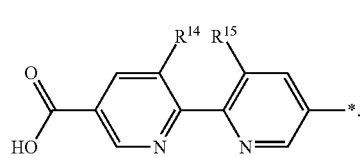

(18)

In Formula (18), $R^{14}$ and $R^{15}$ are selected from hydrogen atom, a hydrocarbon group containing up to three carbon atoms, or a polar group, and can optionally be interconnected, as described under Formula (17).

In a particular embodiment of the seventeenth embodiment, $R^{14}$ and $R^{15}$ are interconnected to form a bridging aromatic ring, thus producing an iron-binding portion having the following structural formula:

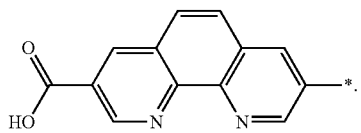
(18a)

In an eighteenth set of embodiments, the iron-binding portion has the following structural formula:

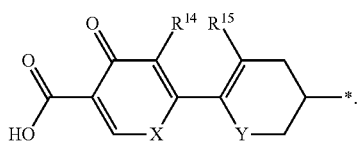
(19)

In Formula (19), X and Y are independently selected from —CH$_2$—, —O—, —S—, or —NR$^4$, wherein R$^4$ is as defined above (typically, —NR$^4$ is —NH—), provided that at least one of X and Y is not —CH$_2$—. In some embodiments, none of X and Y is —CH$_2$—. In other embodiments, one of X and Y is —NH— and one of X and Y is —O—. In other embodiments, both X and Y are —O—, or both X and Y are —NH—.

In a particular embodiment of the eighteenth embodiment, R$^{14}$ and R$^{15}$ are interconnected to form a bridging aromatic ring, thus producing an iron-binding portion having the following structural formula:

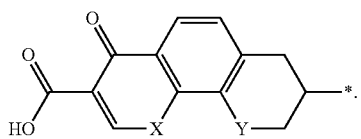
(19a)

In a nineteenth set of embodiments, the iron-binding portion has the following structural formula:

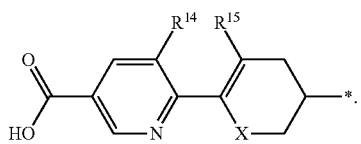
(20)

In Formula (20), R$^{14}$ and R$^{15}$ are selected from hydrogen atom, a hydrocarbon group containing up to three carbon atoms, or a polar group. X in Formula (20) is either —CH$_2$—, —O—, —S—, or —NR$^4$, wherein R$^4$ is as defined above (typically, —NR$^4$ is —NH—). In some embodiments, X is not —CH$_2$—. In some embodiments, R$^{14}$ and R$^{15}$ are not interconnected. In other embodiments, R$^{14}$ and R$^{15}$ are interconnected to form a ring, thereby forming a tricyclic structure in Formula (20).

In a particular embodiment of the nineteenth embodiment, R$^{14}$ and R$^{15}$ are interconnected to form a bridging aromatic ring, thus producing an iron-binding portion having the following structural formula:

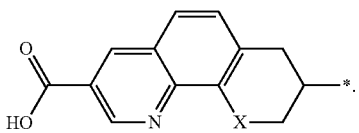
(20a)

In a twentieth set of embodiments, the iron-binding portion has the following structural formula:

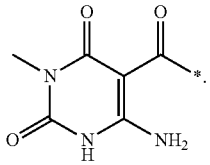
(21)

In Formula (21), the connecting carbon (indicated by asterisk) may be linked to the branched portion of the compound either directly or via a linker, typically up to three or four atom lengths, such as a methylene or ethylene linker.

In a particular set of embodiments, the active compounds considered herein have an iron-binding portion according to Formula (12a), as shown by the following structural formula:

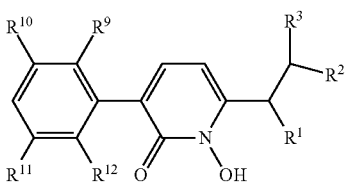
(22)

In Formula (22), R$^1$, R$^2$, R$^3$, R$^9$, R$^{10}$, R$^{11}$, and R$^{12}$ are as described above.

For particular embodiments, any of the classes or particular types of iron-binding portions or branched portions described above can be excluded, or particular classes or types of compounds can be specifically selected by careful delineation of substituents in a generic formula. For example, in particular embodiments, when the iron-binding portion is, or includes, a 8-hydroxyquinolin-7-yl ring system, said 8-hydroxyquinolin-7-yl ring system contains, at least on position 2 thereon, a polar group, particularly a small polar group, such as one selected from —C(O)OH, —OH, halogen atom, and nitro group, as well as methylene-linked versions thereof. In other embodiments, the foregoing provision also applies to a 8-hydroxyquinolin-6-yl ring system. In other embodiments, any 8-hydroxyquinoline ring system in an iron-binding portion is required to contain one, two, or three polar groups on any position of the ring system, particularly on the 2 and/or 3 positions of the ring system. In some embodiments, the foregoing provision applies only to a 8-hydroxyquinolin-7-yl or 8-hydroxyquinolin-6-yl ring system.

In some embodiments, a quinolone ring system is excluded from the iron-binding portion, or, more specifically, a quinolone ring system with carbonyl group on the 2-position of the quinolone ring is excluded, while a quinolone ring system with carbonyl group on other positions (e.g., 3- or 4-positions) may or may not be excluded. In other embodiments, for either a quinolinyl or quinolonyl ring system, the branched portion is attached directly to the quinolinyl or quinolonyl ring system (i.e., attached to a ring carbon or nitrogen atom of any of these systems), i.e., without a linker, or alternatively, without a linker containing three or more linking atoms, and particularly, without a linker containing an amido (i.e., —NHC(O)—) linkage or methylene amido linkage (i.e., —CH$_2$—NH—C(O)— or —CH$_2$—C(O)—NH—). In yet other embodiments, if a quinolonyl ring system is included, the quinolonyl ring system does not include the branching portion on the benzene ring portion of the quinolonyl ring system, and in more particular embodiments, the branching portion is not included specifically on the 6-position of the quinolonyl ring system (and instead located, e.g., on the 5-, 7-, 8-, 3-, or 4-position of the quinolonyl ring system).

The compounds described herein can be synthesized by any methods known in the art. Many of the quinolinyl derivatives described herein, in particular, can utilize the methodology described in the art for their synthesis, along with appropriate modification as would be readily understood in the art. See, for example, N. C. Warshakoon, et al., *Bioorganic & Medicinal Chemistry Letters*, 16, pp. 5517-5522 (2006), the entire disclosure of which is incorporated herein by reference.

Numerous other synthetic methodologies are known and applicable herein, along with appropriate modification, for synthesizing a wide range of compounds encompassed by Formula (1), including quinolinyl, quinolonyl, and imidazopyridinyl compounds. See, for example, N. C. Warshakoon, et al., *Bioorganic & Medicinal Chemistry Letters*, 16, pp. 5598-5601 (2006); J. K. Murray, et al., J. Comb. Chem., 12, pp. 676-686 (2010); International Pub. WO 2007/070359; M. Frohn, et al., *Bioorganic & Medicinal Chemistry Letters*, 18, pp. 5023-5026 (2008); and ACS Med. Chem. Lett., 1, pp. 526-529 (2010); the entire contents of which are herein incorporated by reference.

Some additional generic protocols applicable herein for preparing the quinolinyl or indolyl compounds described herein, along with appropriate modification, are provided in the following synthetic schemes:

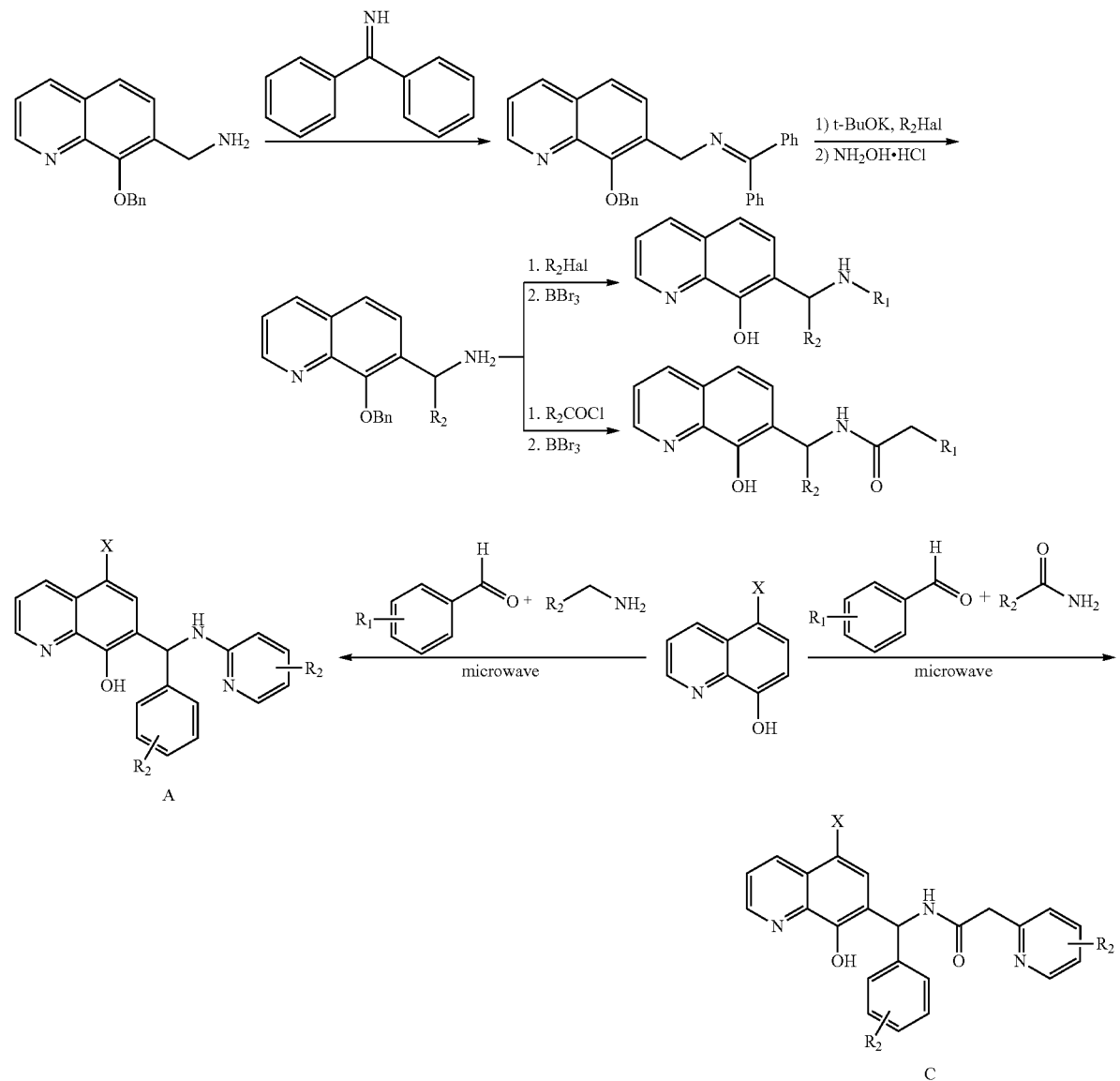

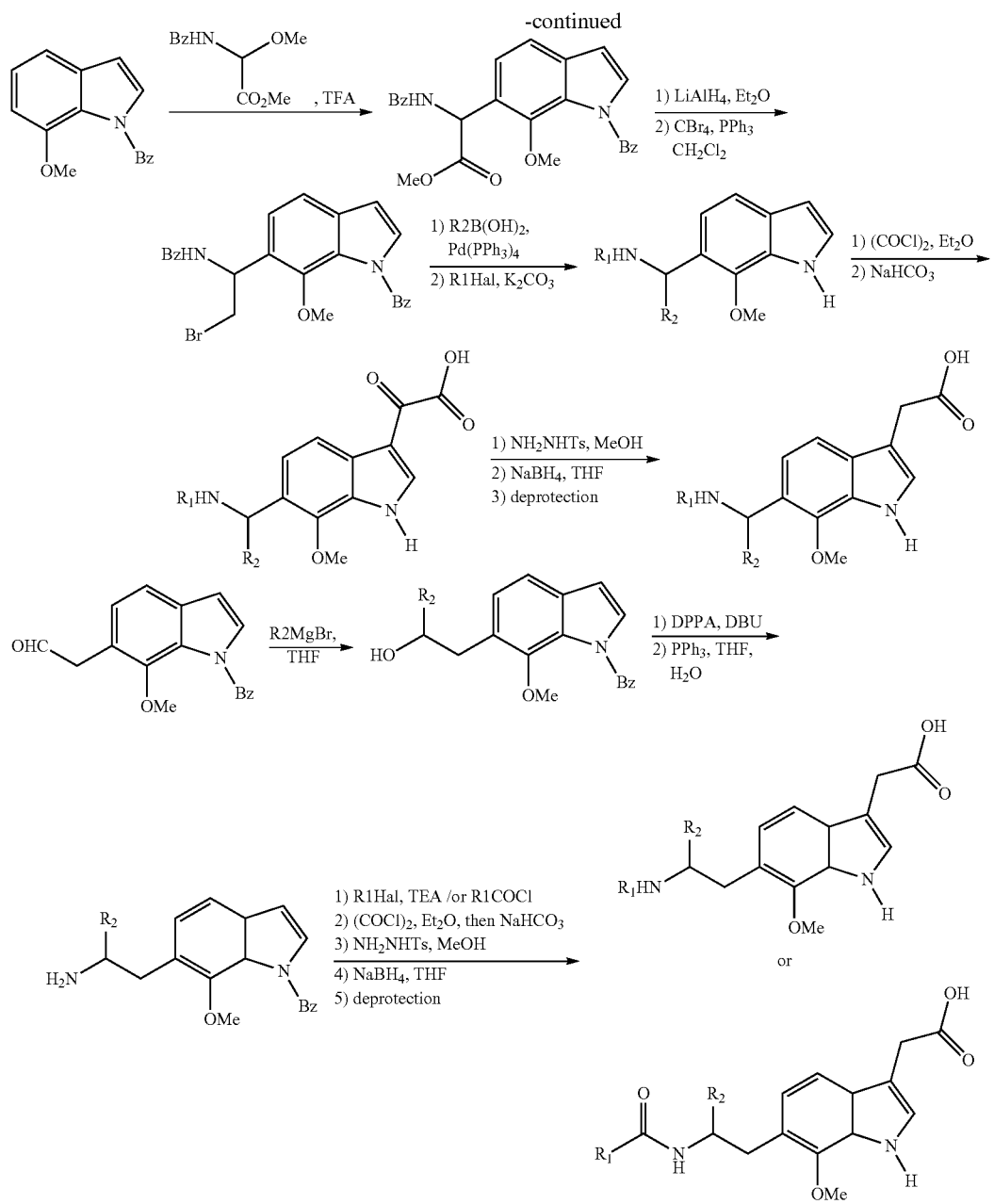

In another aspect, the invention is directed to a pharmaceutical composition that contains any one, two, or more of the above HIF PHD-inhibiting compounds in a pharmaceutically acceptable vehicle (i.e., excipient). The pharmaceutical composition can also be formulated together with one or more medications that improves the overall efficacy of the pharmaceutical composition and/or reduces or avoids side effects.

The active ingredient(s) and excipient(s) may be formulated into compositions and dosage forms according to methods known in the art. As described in detail below, the pharmaceutical compositions of the present invention may be specially formulated for administration in solid or liquid form, including those adapted for the following: (1) oral administration, such as, for example, tablets, capsules, powders, granules, or pastes for application to the tongue, aqueous or non-aqueous solutions or suspensions, drenches, or syrups; (2) parenteral administration, such as, for example, by subcutaneous, intramuscular or intravenous injection as provided by, for example, a sterile solution or suspension; (3) topical application, such as, for example, provided by a cream, ointment, or spray applied to the skin, lungs, or mucous membranes; or (4) intravaginally or intrarectally, such as, for example, as a pessary, cream or foam; (5) sublingually or buccally; (6) ocularly; (7) transdermally; or (8) nasally.

The phrase "pharmaceutically acceptable" refers herein to those compounds, materials, compositions, and/or dosage forms which are, within the scope of sound medical judgment, suitable for administration to a subject. The phrase "pharmaceutically acceptable excipient" as used herein refers to a pharmaceutically-acceptable material, composition, or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic composition for administration to the subject. Each excipient should be "acceptable" in the sense of being compatible with the other ingredients of the formulation and not injurious to the subject.

Some examples of materials that can serve as pharmaceutically-acceptable excipients, particularly for liquid forms, include sugars (e.g., lactose, glucose and sucrose); starches (e.g., corn and potato starch); cellulose and its derivatives (e.g., sodium carboxymethyl cellulose, ethyl cellulose and cellulose acetate); gelatin; talc; waxes; oils (e.g., peanut oil, cottonseed oil, safflower oil, sesame oil, olive oil, corn oil and soybean oil); glycols (e.g., ethylene glycol, propylene glycol, and polyethylene glycol); polyols (e.g., glycerin, sorbitol, and mannitol); esters (e.g., ethyl oleate and ethyl laurate); agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19th Ed. Mack Publishing Company, Easton, Pa., (1995).

Diluents increase the bulk of a solid pharmaceutical composition, and may make a pharmaceutical dosage form that is easier for the patient or caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the subject's stomach may be increased by the addition of a disintegrant to the composition. Some examples of disintegrants include alginic acid, carboxymethylcellulose calcium, carboxymethylcellulose sodium (e.g. Ac Di Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Numerous other auxiliary agents, commonly known in the art, may be included in the pharmaceutical composition. Some examples of these other auxiliary agents include glidants for improving the flowability of a non-compacted solid composition (e.g., colloidal silicon dioxide, magnesium trisilicate, powdered cellulose, starch, talc and tribasic calcium phosphate); lubricants to reduce adhesion during processing (e.g., magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate); liquid carriers or dispersants, such as water, vegetable oil, alcohol, polyethylene glycol, propylene glycol or glycerin; emulsifying agents, such as gelatin, egg yolk, casein, cholesterol, acacia, tragacanth, chondrus, pectin, methylcellulose, carbomer, cetostearyl alcohol and cetyl alcohol; viscosity-enhancing agents to improve the mouthfeel of the product and/or coat the lining of the gastrointestinal tract (e.g., acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum); sweetening agents, such as sorbitol, saccharin, sodium saccharin, sucrose, aspartame, fructose, mannitol and invert sugar; flavoring agents and flavor enhancers, such as maltol, vanillin, ethyl vanillin, menthol, citric acid, fumaric acid, ethyl maltol and tartaric acid; preservatives and chelating agents, such as alcohol, sodium benzoate, butylated hydroxy toluene, butylated hydroxyanisole and ethylenediamine tetraacetic acid; buffers, such as gluconic acid, lactic acid, citric acid or acetic acid, sodium gluconate, sodium lactate, sodium citrate or sodium acetate. The selection of excipients and the amounts used may be readily determined by the formulation scientist based upon experience and consideration of standard procedures and reference works in the field.

In another aspect, the invention is directed to methods for treating a patient having a condition that would benefit from inhibiting HIF PHD. The method includes administering to the patient an effective amount of any of the HIF PHD-inhibiting compounds described above, typically by administration of a pharmaceutical composition containing one or more HIF PHD-inhibiting compounds. The treatment may be administered when hypoxic damage is evident, or alternatively, as a preventative treatment before hypoxic damage is evident.

In some embodiments, the HIF PHD-inhibiting compounds being administered possess a minimum level of HIF-activating ability, herein also referred to as a percent (%) activation. For example, in some embodiments, the compounds being considered for administration have at least or greater than 30, 40, 50, 60, 70, 80, 90, 95, 100, 110, or 120% activation. The % activation values provided herein are generally in comparison to ciclopirox as a standard. After a subsequent concentration titration, $EC_{50}$ values can be determined. For the compounds described herein, and particularly, the quinoline compounds, the $EC_{50}$ value is generally no more than (or below) 2 µM. In some embodiments, the $EC_{50}$ value for compounds described herein, and particularly, the quinoline compounds, is no more than (or below) 1.8, 1.5, 1.3, or 1.0 µM. In cellular models, the efficacy of the compound is typically measured as an activation (fold) over the control, for a HIF1 target gene, such as VEGF. Biological efficacy is generally determined as fold activation of HIF1 target genes. Typically, the fold activation is more than 2 (i.e., 2-fold). In some cases, the fold activation is precisely, or at least, 3-fold, 4-fold, 5-fold, 6-fold, 7-fold, 8-fold, 9-fold, 10-fold, or even 15-fold.

In one embodiment, the composition is administered to the patient in such a manner that the composition does not specifically target particular tissue or cells of the body. The composition can be administered non-specifically by, for example, injection into the blood stream. In another embodiment, the composition is administered to the patient in such a manner that the composition selectively targets particular tissue or cells of the body. The composition can be made to selectively target particular tissue or cells within a mammal by, for example, administering the composition in a localized manner at the site of target tissue or cells (for example, by injection into target tissue or cells). In an alternative embodiment, the composition can be made to selectively target particular tissue or cells within a mammal by administering the composition non-locally or locally, and including in the composition a selective targeting agent that selectively targets certain tissues or certain cells of the body (e.g., by employing an antibody targeting agent). The tissue being treated can be, for example, tissue of the heart, kidneys, liver, bone marrow, pancreas, spleen, skin, lungs, nerves (particularly of the peripheral nervous system), eyes (e.g., retina), muscles, and brain, and any other tissue that may suffer from, or be at risk for, hypoxic damage.

The result of the therapy is that HIF PHD is at least partially or substantially inhibited in order to treat or prevent adverse conditions that result from non-optimal or excessive suppression or delayed onset of the cellular HIF response, typically expressed as hypoxic damage. Some examples of conditions that can be treated include anemia, ischemia, retinal degeneration, cardiovascular hypoxic conditions (e.g., myocardial infarction), and neurodegenerative diseases. The ischemia can be any of the ischemic conditions known in the art for which HIF PHD inhibition can be beneficial. For example, in particular embodiments, the ischemia is in the cardiovascular system (e.g., ischemic heart disease), or is associated with anti-cancer treatment (e.g., as a side effect of medical treatment or the cancer itself), or is associated with kidney malfunction (e.g., ischemic kidney malfunction). The neurodegenerative disease can be any of the neurodegenerative diseases or conditions in the art for which HIF PHD inhibition can be beneficial. For example, in particular embodiments, the neurodegenerative disease is associated with Parkinson's or Huntington's disease.

In order to realize the therapeutic effect of HIF PHD inhibition, the HIF PHD-inhibiting compound is administered in a therapeutically-effective amount. As is well known in the art, the dosage of the active ingredient(s) significantly depends on such factors as the extent of the hypoxia, method of administration, size of the patient, and potential side effects. In different embodiments, depending on these and other factors, a suitable dosage of the active ingredient may be precisely, at least, or no more than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, per 50 kg, 60 kg, or 70 kg adult, or a dosage within a range bounded by any of the foregoing exemplary dosages. Depending on these and other factors, the composition is administered in the indicated amount by any suitable schedule, e.g., once, twice, or three times a day for a total treatment time of one, two, three, four, or five days, and up to, for example, one, two, three, or four weeks. The indicated dosage may alternatively be administered every two or three days, or per week. Alternatively, or in addition, the composition is administered until a desired change is evidenced.

Examples have been set forth below for the purpose of illustration and to describe the best mode of the invention at the present time. However, the scope of this invention is not to be in any way limited by the examples set forth herein.

EXAMPLES

In a high throughput screen (HTS), there has been discovered herein a novel class of HIF PHD-inhibiting compounds comprising catechol and oxyquinoline iron-binding units derivatized with a previously undescribed "branching motif", immediately adjacent to the iron-binding motif in the compound.

For HTS, a cell-based reporter system was employed. The cell-based reporter system was generated by fusing HIF-1a oxygen degradable domain (ODD) to luciferase (Safran M. et al., PNAS, 2006, 103, 105-110), which represents a cell-based capture assay monitored by the consumption of the luciferase-labeled HIF substrate under the conditions more physiological than in vitro test tubes. In accord with their structure activity relationship in reporter assay, the best "hits" stabilize HIF1, upregulate known HIF target genes in a human neuronal line, and exert neuroprotective effects in established model of oxidative stress in cortical neurons.

Development and Optimization of the Odd-Luc Reporter System

Figure 1B:
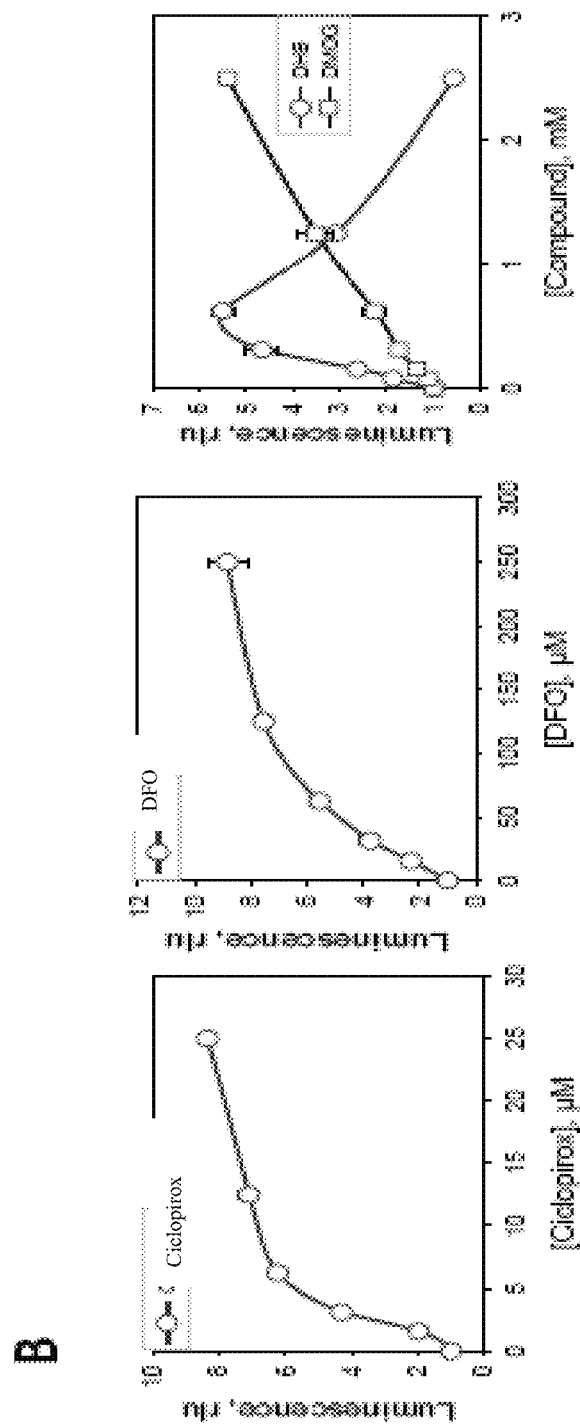

The reporter cell lines constitutively expressing ODD-luc (human neuroblastoma, SH-SY5Y) were stable for more than one year without significant change in their response to canonical PHD inhibitors such as DFO, dihydroxybenzoate (DHB), dimethyloxalylglycine (DMOG), and ciclopirox (FIG. 1B). In order to verify the specificity of luciferase changes as an assay for PHD activity, several control lines were developed: the control line expressing ODD-luc with proline 564 and 567 mutated to Ala generates luciferase fusion that cannot be degraded and experimentally identifies a ceiling level of ODD-luc protein attainable in these cells. The background signal for the wild-type HIF ODD-luc line (PYIP) corresponds to approximately 5-6% of the ODD-luc levels in the control line AYIA (double mutant P564A/P567A line) (FIG. 2). Treatment with 10 µM ciclopirox results in a 10-fold increase of a background signal for the wild-type ODD-luc reporter (PYIP line), i.e. reaches almost 50% of the threshold value (FIG. 2). These particular conditions are ideal for HTS as they promote the selection of both weaker and more potent inhibitors than ciclopirox.

Figure 8:
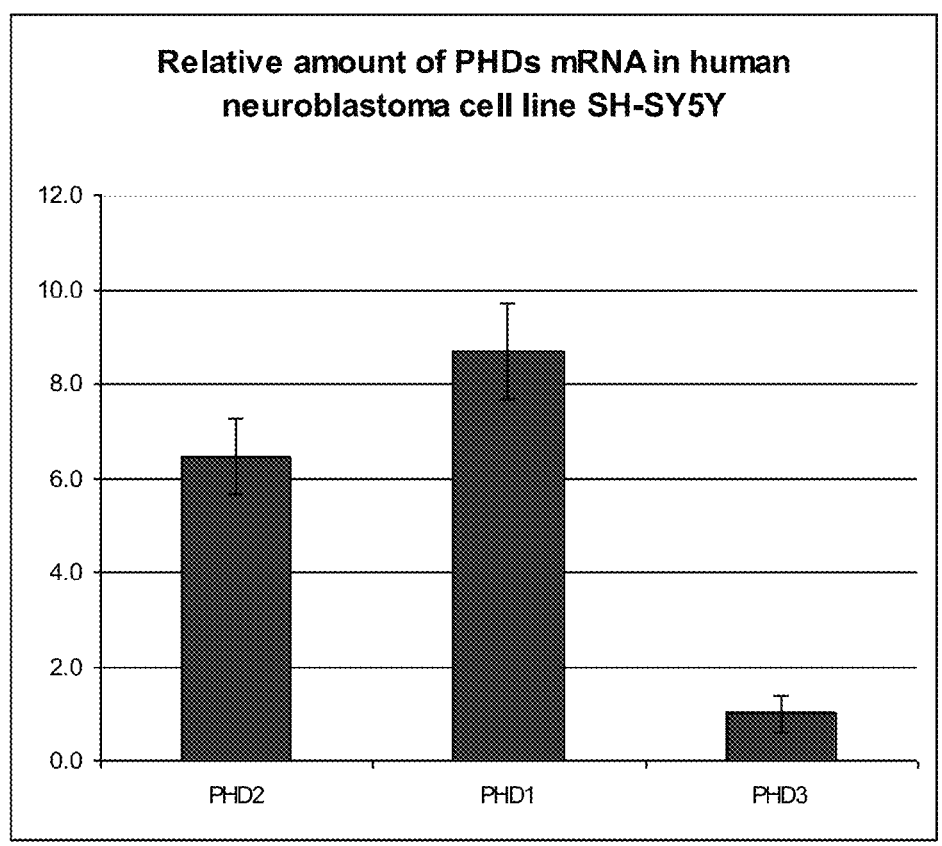
FIG. 8. PHD1 and PHD2 are major enzyme isoforms in human neuroblastoma cell line.
Figure 11:
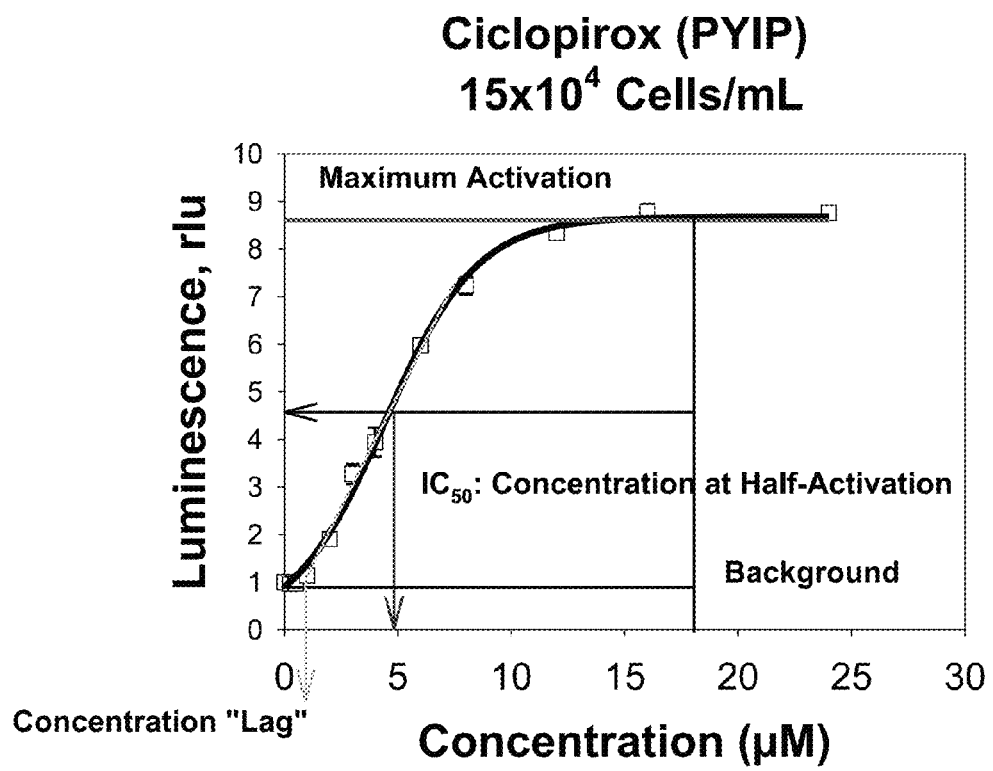
FIG. 11. Determination of activation parameters from a concentration titration curve.

The neuroblastoma cell line expresses all three PHD isoforms (FIG. 8). In the second control line, as an initial test of fidelity of the constructs for reporting endogenous regulation, Tyr565 was mutated to Ala, which has been previously shown to decrease the affinity of HIF for PHD2 (Bruick et al., Science 294, 1337-1340 2001; Jaakkola P., et al., Science 292, 468-472 2001; Landazuri, M. O., et al., Biochem Biophys Res. Commun. 351, 313-32 2006). As expected, line PAIP shows a 3-4-fold higher steady state level of ODDluc than the wild type line (FIG. 2). Of note, the third control, mutation of Pro567 to Ala, which has been shown to influence recognition of the HIF ODD by PHD3 (Landazuri, M. O., et al., Biochem Biophys Res. Commun. 351, 313-32 2006), has lesser effect on ODD-luc levels (FIG. 2). The fact that the reporter system is sensitive to single-point mutations surrounding Pro564 region in accord with previously published observations (Bruick et al., Science 294, 1337-1340 2001; Jaakkola P. et al., Science 292, 468-472 2001; Landazuri, M. O., et al., Biochem Biophys Res. Commun. 351, 313-32 2006) provides evidence that the rate-limiting step is controlled by the PHD catalyzed reaction.

Figure 3A:
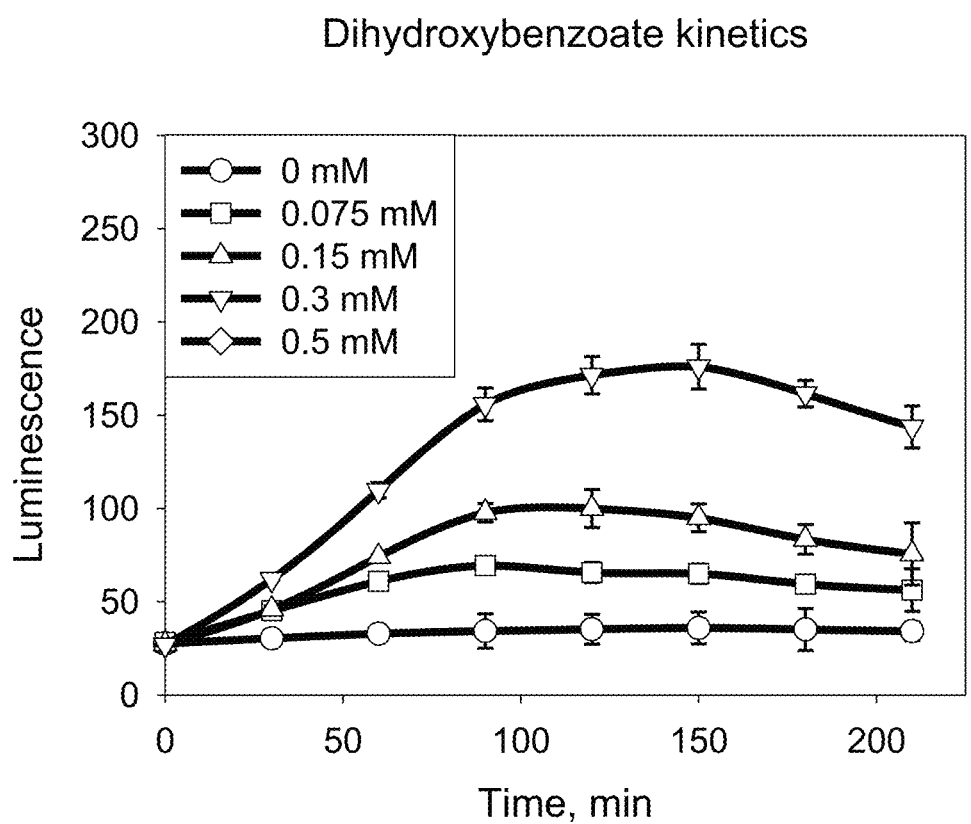
FIG. 3. Determination of apparent HIF PHD inhibition constants from time course of reporter activation. (A) original kinetic curves; (B) determination of promoter capacity, $K_o$, i.e. the maximum of rate of fusion accumulation using saturated concentrations of ciclopirox; (C) linear plot to calculate the apparent inhibition constants using Equation 3.

The HIF ODD-luciferase reporter system is controlled by the rate of PHD catalyzed reaction, and from an enzyme kinetics point of view, it is a "capture assay" monitored by the consumption of a substrate, the heterologously expressed HIF ODDluciferase fusion protein. In the kinetic regime, i.e. monitoring the time-course of luminescence changes (FIG. 3A), the ODD-luc reporter system permits quantitative characterization of promoter capacity (Ko, rate of fusion protein generation), enzyme activity, and inhibition constant determination.

The rate of fusion accumulation equals the rate of its production ($K_o$) minus the rate of the rate-limiting step, controlled by HIF PHDs, which obeys Michaelis-Menten kinetics, as follows:

$$v=d[\text{ODDluc}]/dt=K_0-k_1[\text{PHD}][\text{ODDluc}]/\{K_m(1+[\text{I}]/K_1)+[\text{ODDluc}]\} \quad \text{(Eq.1)}$$

wherein $K_m$ is the inhibition constant for a competitive inhibitor, $k_1$ is rate coefficient, [PHD] and [ODD-luc] are the concentrations of the enzyme and substrate, respectively.

The background luminescence signal calibrated with recombinant luciferase allows an estimation of the steady-state concentration of the ODD-luc fusion protein. Under the conditions used the steady-state value of 60 rlu (relative light units) corresponds to 1 pg luciferase protein; dividing this number by the total cell volume taken as a single cell volume ($233\mu^3$) multiplied by 30,000 cells/well density (number of cells in a 96 well dish), the ODD-luc fusion protein steady-state concentration is found to be equal to 2.3 nM, which is well below all reported Km values for HIF1 (Dao, J. H., et al., Anal Biochem 384, 213-223 2009; Hewitson, K. S., et al., Methods Enzymol 435, 25-42 2007; Koivunen, P., et al., J Biol Chem 281, 28712-28720 2006; Tuckerman, J. R., et al., FEBS Lett 576, 145-150 2004. Therefore, it is preferable to work under nonsaturating conditions with respect to HIF substrate, i.e. optimal conditions for selecting inhibitors competitive against HIF substrate. Moreover, as compared to the in vitro assay, which uses a 19 amino acid peptide fragment surrounding the oxygen dependent domain (ODD), the instant ODD-luciferase construct contains 123 amino acid acids, and thus, more closely emulates the behavior of native HIF. The initial concentration of fusion can be considered much lower than $K_m$, and thus, can be ignored in the rate equation:

$$v=d[\text{ODDluc}]/dt=K_0-k_1[\text{PHD}][\text{ODDluc}]/K_m(1+[\text{I}]/K_1) \quad \text{(Eq.2)}$$

Figure 3B:
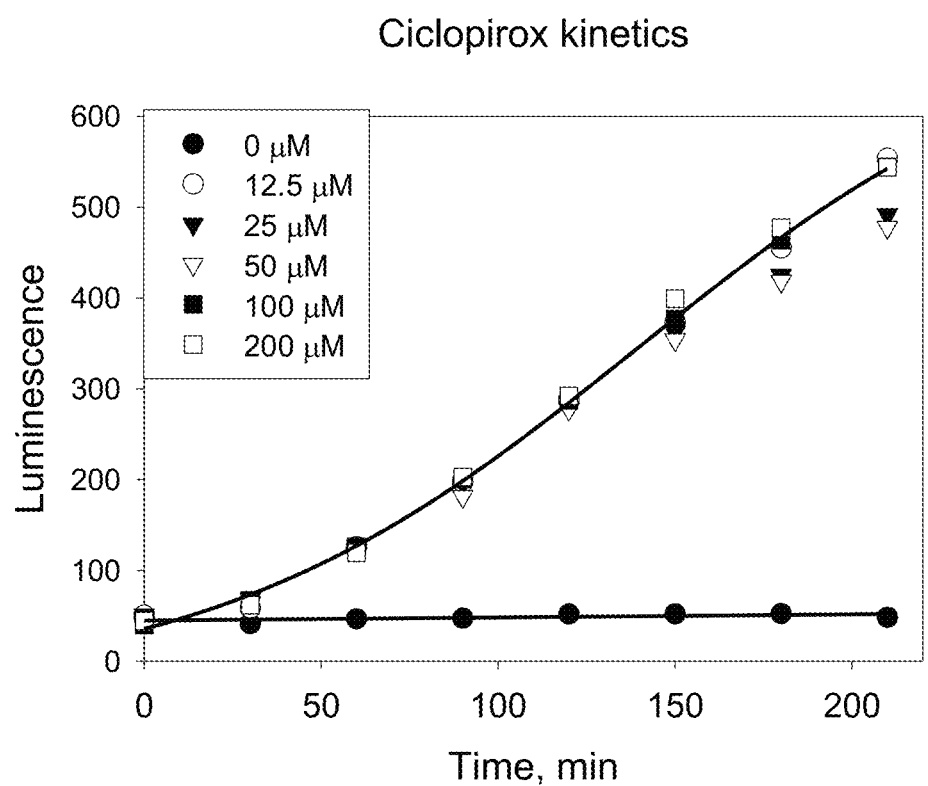
Figure 3C:
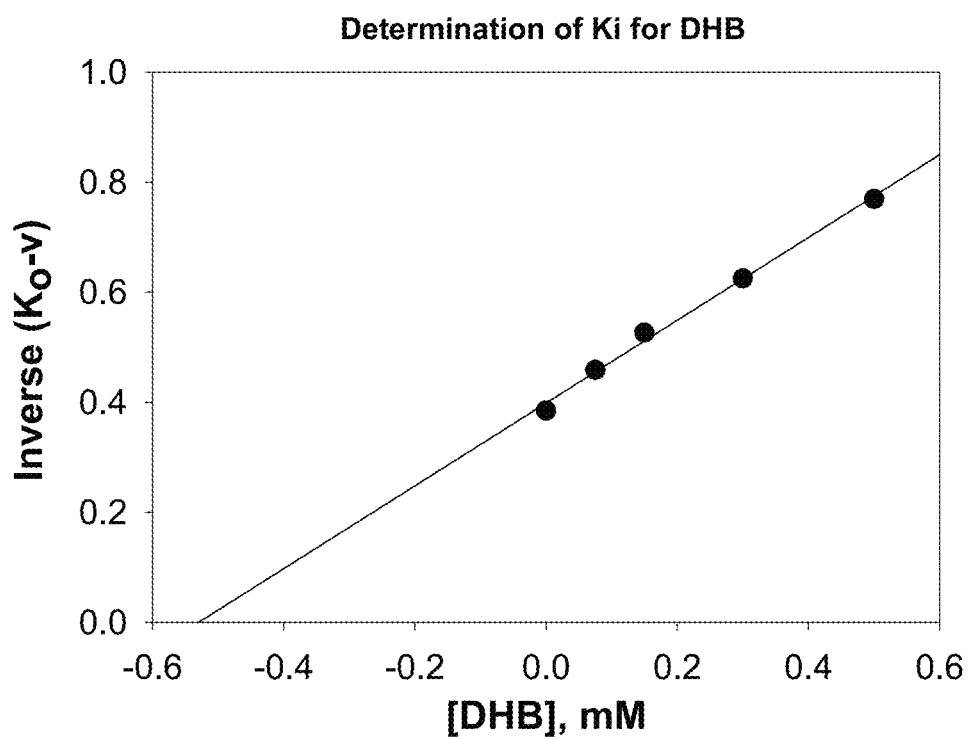

Knowing the capacity of the promoter, the inhibition constant can be determined, but not the inhibition type, from the initial rates of signal accumulation at varied fixed concentrations of potential inhibitor. The capacity of promoter, $K_O$ can be determined under the conditions of total inhibition of PHD activity by means of complete iron deprivation achieved in the presence of high concentrations of ciclopirox, i.e. when the increase in the ciclopirox concentrations give no further increase in the rate of luciferase signal growth (FIG. 3B). The intracellular enzyme activity ($k_1[\text{PHD}]/K_m$) can be also determined by dividing the rate of fusion protein accumulation by the steady-state concentration of the fusion protein determined directly from one and the same experiment in luciferase units, without recalculation for the cellular volume, and corresponds to 0.05 min$^{-1}$. The linear plot of $1/(K_0-v)$ versus the inhibitor concentration gives the value of the apparent inhibition constant as the intercept on X-axis (FIG. 3C):

$$1/(K_0-v)=K_m(1+[\text{I}]/K_1)/k_1[\text{PHD}][\text{ODDluc}]_0 \quad \text{(Eq.3)}$$

The apparent inhibition constant determined for DHB and DMOG is 0.52 mM and 1.3 mM, respectively, which is in agreement with previous observations on their biological effects exerted in the millimolar range (Asikainen, T. M., et al., Free Radic Biol Med 38, 1002-1013 2005; Lomb, D. J., et al., Mol Pharmacol 75, 1198-1209 2009; Philipp, S., et al., Am J Physiol Heart Circ Physiol 290, H450-457 2006) and IC$_{50}$ reported for PHD2 in vitro assay (Cho, H., et al., Biochem Biophys Res. Commun., 337, 275-280 2005).

The response of the ODD-luc reporter to canonical HIF PHD inhibitors, and the increased stability of single-point mutant reporters in accord with the predictions, provided confidence that this system could be utilized for screening for novel small molecule HIF PHD inhibitors. Hence, conditions were optimized for high throughput screening.

A Primary Screen Identified 160 Validated Hits

The screen of 85,000 compounds library (including those from Spectrum, ChemDiv, AMRI, ChemBridge. Prestwick and Cerep) resulted in 295 hits, among which 160 were confirmed in follow up testing. Of note, no established proteasomal inhibitors were identified in the screen. Hits were then classified into 10 structural clusters, six of which are shown in FIG. 4A.

Hydrazides and hydrazones: Among this chemical group (55 hits of 76 hydrazides and hydrazones tested) are well-established HIF activators [e.g., U.S. Pat. No. 6,660,737] that form a tight 2:1 6-coordinated Fe complex in solution but not within the enzyme. It is likely that global cellular iron deprivation emerging from these compounds results in reporter activation comparable or even higher than that for ciclopirox. Interestingly, a group of edaravone hydrazone derivatives was identified that can provide only two iron ligands, such as (Z)-1,3-diphenyl-4-(thiazol-2-ylhydrazono)-1H-pyrazol-5(4H)-one (I) (FIG. 4A) and (Z)-4-(benzo[d]thiazol-2-ylhydrazono)-1,3-diphenyl-1H-pyrazol-5(4H)-one, and unlike other members of the class which bind iron outside the enzyme these may coordinate iron inside the enzyme. However, the level of reporter activation for the two iron ligand edaravone derivatives is lower (86% and 70%, respectively) than for hydrazones providing three iron ligands (above 100%). Of note, edaravone has been used in Japan to treat humans with stroke [Kikuchi, K., et al., J Pharmacol Exp Ther 329, 865-874 (2009a); Kikuchi, K., et al., Biochem Biophys Res Commun (2009b]. However, edaravone itself does not provide iron ligands and shows no reporter activation.

Hydralazine, an FDA approved anti-hypertensive agent, is known to be a HIF stabilizer [Knowles, H. J., et al., Circ Res 95, 162-169 (2004); Michels, C., et al., World J Urol (2009)] and an activator of a hypoxia response element (HRE)-luc reporter [e.g., WO/2007/048004; 60/729,059]. The data also implicate a hydralazine analog, (2-hydrazinyl-4,6-diphenylpyrimidine) (II) (FIG. 4A) as a potent HIF stabilizer (64% or 6.7-fold activation). The presence of a terminal amino group and free rotation of phenyl rings (ortho-hydroxy group in one ring abolishes activation effect) appear to be required for the activation effect observed. The compound exhibits no iron chelation properties in solution.

Dibenzoylmethanes (DBM): Two compounds were identified that exhibit a similar docking mode to DBM, another established HIF activator [Mabjeesh, N. J., et al, Biochem Biophys Res Commun, 303, 279-286 (2003)]. The sulfur-containing analog of DBM (III) (FIG. 4A) resulted in a five-fold (or 41% of ciclopirox) reporter activation.

Thiadiazoles: Thiadiazole compounds (4 hits out of 8 compounds tested) provide modest activation (3-5-fold activation or 25-40% of the internal standard, FIG. 4A, IV) and have a number of potential iron ligands which may support two modes of the compound docking into the PHD2 active site in place of αKG. In either case, the predicted interference from "bulky" attachments at the amide end is in agreement with experimental observations: 2-amino-N-(5-(4-bromophenyl)-[1,3,4]thiadiazol-2-yl)-3-methylpentanamide and 2-amino-N-(5-(4-methoxy-phenyl)-[1,3,4]thiadiazol-2-yl)-3-phenylpropanamide show no reporter activation at all.

Isoquinolinotriazolylthiols: This class of compounds likely stabilized ODD-luc in the instant assay via their iron chelation in solution. Iron chelation by isoquinolinotriazolylthiols (V) (FIG. 4A) depends on their ability to provide two iron ligands and depends on the rotation restriction between isoquinoline and triazole rings.

Activation drops by three fold with substitutions at position 4 of the thiazole ring and with "bulky" attachments like meta-, and para-substituted phenyl rings or benzyl substituent containing a methyl branch. Two of 8 hits (5-isoquinolin-1-yl-4-(2-trifluoromethyl-phenyl)-4H-[1,2,4]triazole-3-thiol and 4-isopropyl-5-isoquinolin-1-yl-4H-[1,2,4]triazole-3-thiol (V) (FIG. 4A) show reporter activation close to that for the internal standard, ciclopirox. The activation effects were consistent with the predicted substitution effects on iron chelation ability, therefore this group is likely to act through iron chelation rather than iron coordination in the active center.

Flavonoids are HIF activators [Wilson, W. J., et al., Biochem Biophys Res Commun 293, 446-450 (2002); Jeon, H., et al., Mol Pharmacol 71, 1676-1684 (2007)], but their mechanism of action remained obscure and no structure activity relationships (SAR) have been described for this class of compounds. The 85,000 compound library had 80 flavones (20 of which were hits), 90 isoflavones (7 of which were hits), and 16 flavanones (6 of which were hits). The SAR studies for flavone/isoflavone/flavanone family have been completed and structural requirements for optimal docking have been formulated. In particular, the absence of substitutions in the phenyl ring for 3-hydroxyflavone derivatives appears to be required for optimal docking and reporter activation, while the presence of hydroxy-, or methoxy-groups in the phenyl ring of 5-hydroxyflavones (as well as isoflavones and flavanones) also appears to be required for optimal docking and reporter activation.

Chalcones, precursors for flavones, were also hits screen (the best one found is 2'β-dihydroxychalcone showing 7.5-fold activation or 71%). All provide at least two iron ligands but are unlikely to be useful as biological tools or drugs as they show rather high toxicity compared to flavones. Of the active coumarines (2 active out of 36 tested), both contain a strong iron binding motif, vicinal hydroxyls, and are well-known for forming tight iron complexes. Their size allows binding inside the PHD active site, while coumarines with "bulky" attachments show no reporter activation.

Catechols: The catechol (3,4-dihydroxyphenyl) moiety was found in 100 compounds tested (excluding flavones & coumarins), however, only eight among them were hits. Ethyl-3,4-dihydroxybenzoate is a known PHD inhibitor, which activated the reporter at concentrations 5-fold higher (>50 μM, see FIG. 1B) than the standard screening concentration of 10 μM. L-Dopa, but not D-dopa, carbidopa, dopamine and other analogs tested, was a modest hit (21% or 3-fold reporter activation, $IC_{50}$=15 μM). This finding is of potential interest given the recent data suggesting a protective effect for Sinement (L-dopa and carbidopa) in Parkinson's disease [Warshakoon, N.C., et al., Bioorg Med Chem Lett 16, 5687-5690 (2006); Warshakoon, N.C., et al., Bioorg Med. Chem. Lett. 16, 5517-5522 (2006); Warshakoon, N. C., et al., Bioorg Med Chem Lett 16, 5616-5620 (2006); Warshakoon, N.C., et al., Bioorg. Med. Chem. Lett. 16, 5598-5601 (2006)]. Thioxothiazolidinones (VI) (FIG. 4A) exhibited rather modest reporter activation (35-45% or 4-5-fold). Most intriguing was the identification of four hits containing a branching motif that, in in vitro models, screens the entrance to the active site (two of them are shown in FIG. 9).

Oxyquinolines (22 hits out of 66 compounds tested) could be classified into four groups, among those one could be further divided into three subgroups (VII A-D, FIG. 4A). Oxyquinoline derivatives are established inhibitors of HIF prolyl hydroxylase. They appear to act by providing two ligands for iron binding and thus inhibit PHD2 in vitro with an $IC_{50}$ above 3 μM [Warshakoon, N.C., et al (2006), Ibid.]. Compounds from group A, such as chloroacetoquinoline, exhibit reporter activation comparable to 8-hydroxyquinoline itself (4-5-fold reporter activation or 35-45%), and its halogenated derivatives such as iodoquinol, broxyquinoline, clioquinol [Choi, S. M., et al., J Biol Chem 281, 34056-34063 (2006)], and chloroxine. Clioquinol is of particular interest given its established salutary effects in models of Alzheimer's disease and Huntington's disease and its serious consideration for late stage human trials [Kaur, D., et al., Neuron 37, 899-909 (2003).; Adlard, P. A., et al., Neuron 59, 43-55 (2008)]. For the oxyquinolines, the reporter signal drops with the increased size of the R group. By contrast, it was herein found that oxyquinoline derivatives containing a branched substitution at position 7 (VII D, FIG. 4A), as well as their conformationally constrained analogs (group C) with reasonably short but flexible linkers are the best compounds that result in reporter activation comparable or superior to ciclopirox (see table in FIG. 10). For optimal HIF activation, either halogen or $NO_2$ group at position 5 ($R_3$) is favorable, while any substitution at position 2 (group B) is not tolerated. The binding mode of hydroxylated HIF peptide (FIG. 4B) gives a strikingly similar position of Tyr565 against αKG-binding plane to that of hydroxy-phenyl ring against the oxyquinoline plane in the best hit, i.e., compound 8 (FIG. 4C). This finding provided further impetus to study the effects of branched oxyquinolines in further detail.

Structure-Activity Studies for Selected Branched Oxyquinolines

To further explore the most promising hits, a methodology was developed to discriminate between specific inhibition of PHD and non-specific iron chelation. It was assumed that, if there is no specific interaction between the enzyme and iron-binding inhibitors, the enzyme inhibition constants (or in the instant case, $IC_{50}$) will change in parallel with the iron-binding constants. Specific inhibitors, i.e., those coordinating iron directly at the PHD active site, should deviate ("pop-up") from the group of iron chelators with the same affinity and exhibit better inhibition constants ($IC_{50}$) than those that simply bind iron. The apparent iron binding constants were determined in solution for a dozen of hits of interest (Table in FIG. 7). In addition, the rate constant for association were determined from the kinetics of calcein displacement from its complex with iron ($k_a$), which characterizes how fast oxyquinoline binds iron (Table in FIG. 7). The apparent iron binding constant $K_{Fe}$ for the compounds studied varies more than one order of magnitude, from 0.08 to 2.0 μM, in parallel with the changes in the association rate constant (from 20 to 250 $M^{-1}s^{-1}$), while the dissociation rate constant is barely affected.

The dependence of the ODD-luc reporter signal on inhibitor concentration has a sigmoid shape (FIG. 1B and FIG.

11), which is characterized by maximum activation, $IC_{50}$ and a "concentration lag", which is likely reflects the presence of iron in the media, which can bind drug and delay or impede its intracellular effects. The concentration of iron in the serum used for neuroblastoma cultivation is 1.5 µM.

The studied oxyquinolines can be divided into three groups with respect to their iron binding ability: first, those close to that of ciclopirox (compounds 1,2,4,7,10,13), second, those similar to oxyquinoline (6,8,11,12), and third, very poor iron chelators (3,5,9) showing very poor reporter activation. The best inhibitors are found among the first two groups.

Figure 12:
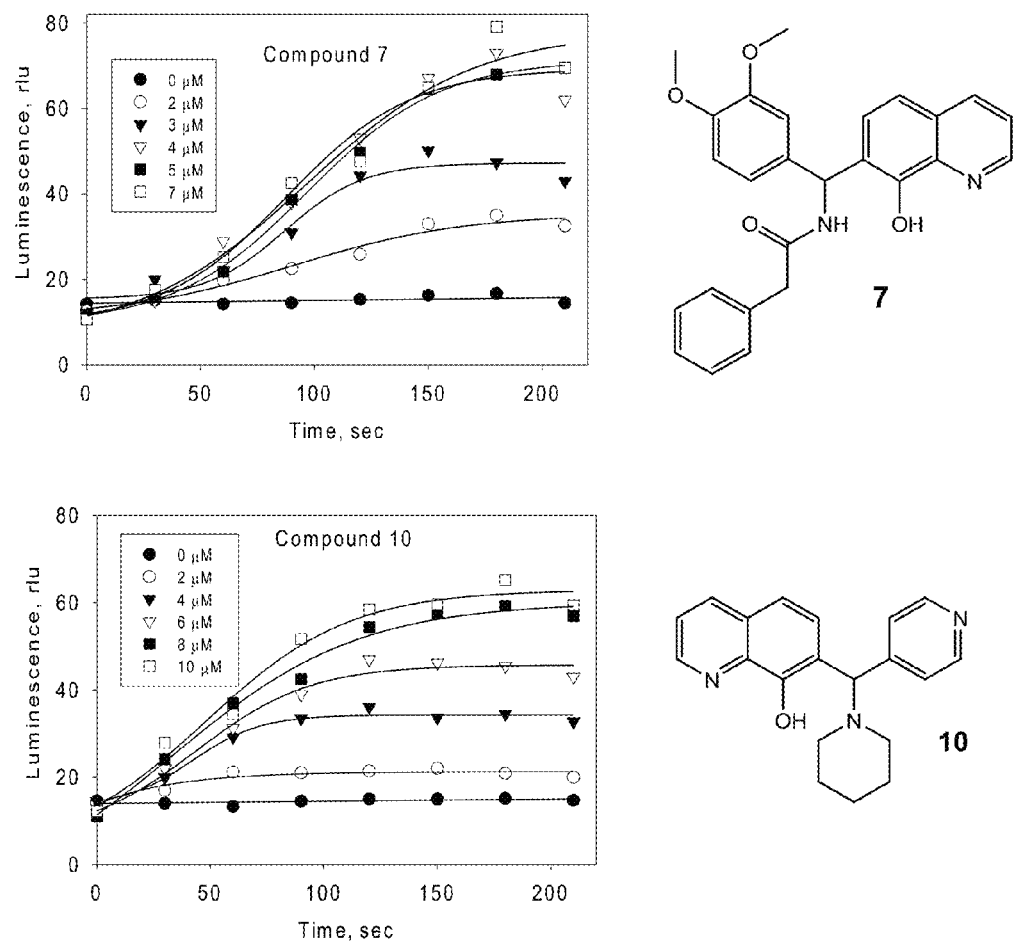
FIG. 12. Comparison of kinetics of reporter activation for good (7) and bad hits (10). 10,000 cells per well.

The table in FIG. 7 clearly points to five compounds as reporter activators better than ciclopirox: compound 8 belongs to the D2 group, while all others (1,4,6,7) belong to the D3 group. The comparison of iron binding and reporter activation parameters (The table in FIG. 7) shows no direct correlation between chelation ability of oxyquinolines and $IC_{50}$ for PHDs; thus, it appears that a requirement for good activation is the absence of 2-methyl group in oxyquinoline ($R_4$) and dioxol group in the phenyl ring $R_1$. The absence of a linker, i.e. immediately attached branched motif to the position 7 of oxyquinoline (10, the table in FIG. 7), is good for iron chelation, but not for reporter activation. The reduced efficacy of compound 10 in the reporter assay is not related to poorer cell membrane permeability. Indeed, compound 10 activates the reporter much faster than compound 7 (see kinetics of reporter activation for both compounds in FIG. 12). In conclusion, it appears that structural determinants, and not iron binding constants, play a more significant role in reporter activation.

Biological Effects of Best Branched Oxyquinoline Hits

Figures 5A, 5B:
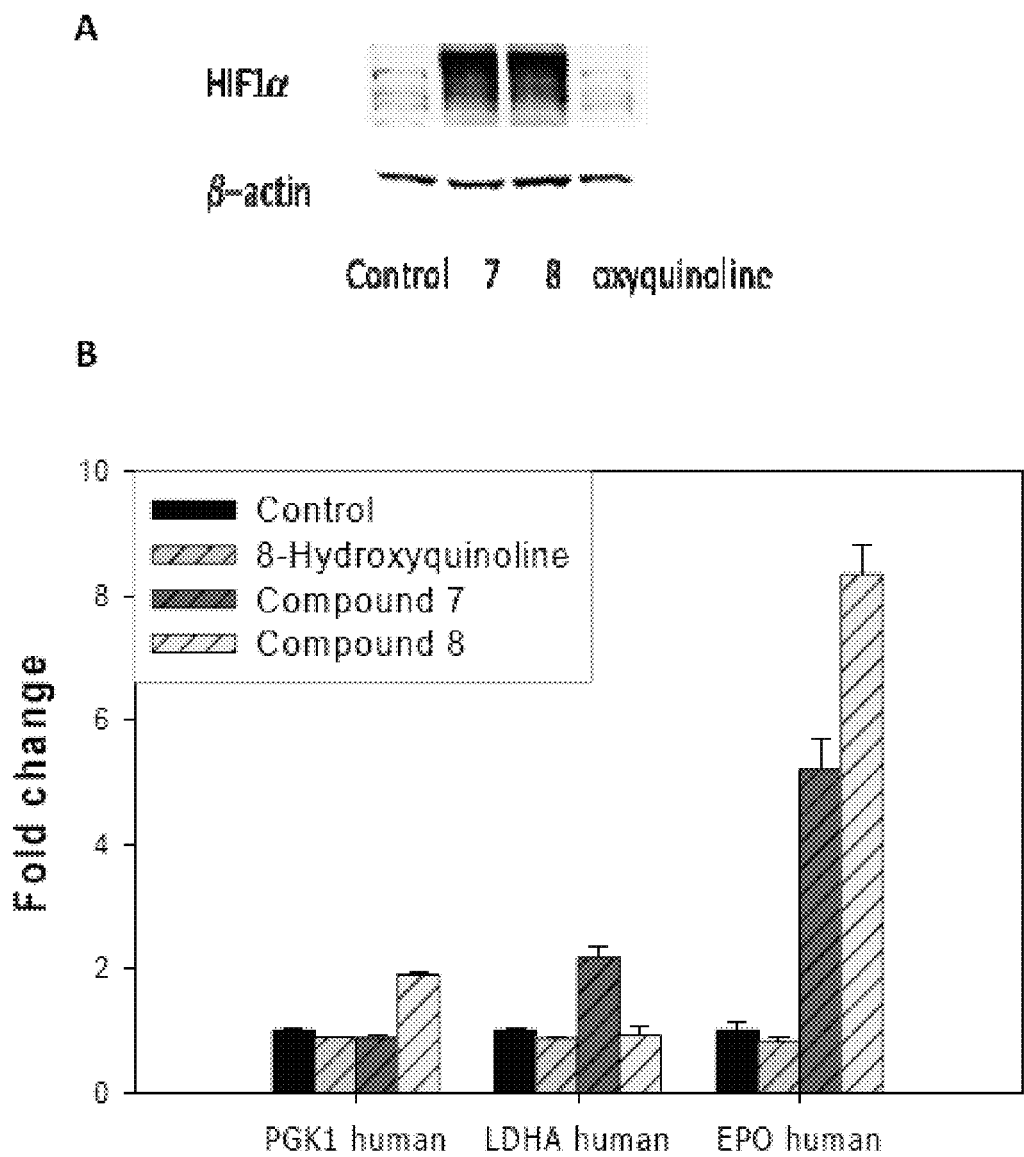
FIG. 5. Upregulation of HIF1a (A) and HIF-regulated human genes, e.g. Epo, PGK1, LDHA (B) upon three-hour treatment of neuroblastoma cells with 5 µM inhibitor.
Figure 6A:
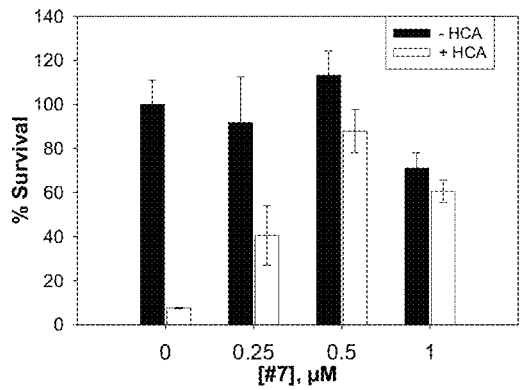
FIG. 6. Neuroprotection effects of best branched oxyquinoline hits (7,8) in comparison with a poor hit from the same group (10) in oxidative stress (HCA) model: (A, B, C) Concentration titrations for compounds (7), (8) and (10), respectively; (D) photographs of viability test for 0.6 µM for (8) and (10).
Figure 6B:
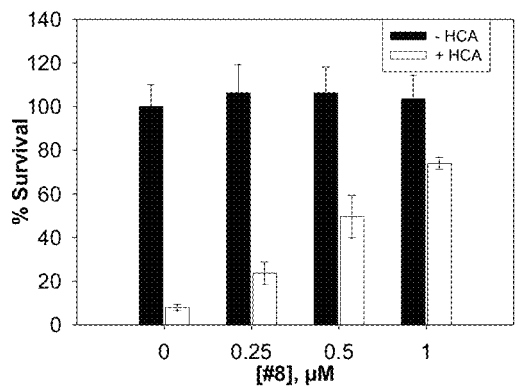
Figure 6C:
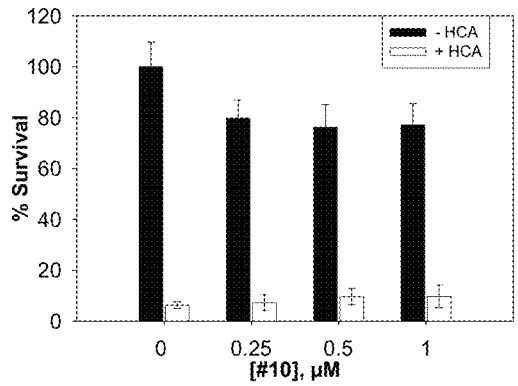
Figure 6D:
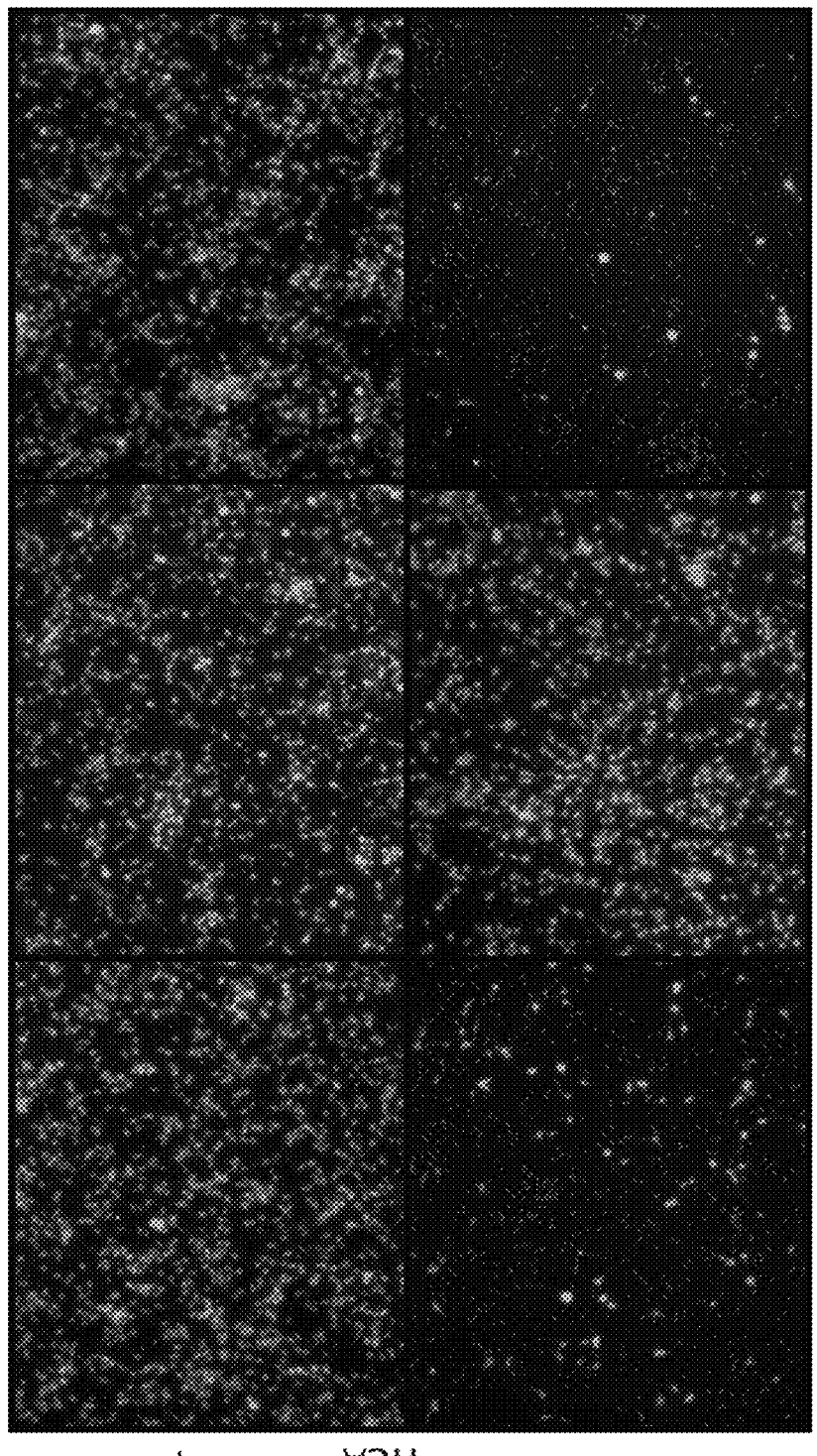

To verify that reporter activation corresponds to the biological effects exerted by branched oxyquinolines, compounds 7 and 8 were selected as positive controls, and oxyquinoline and compound 10 as negative controls. As expected, the best hits (compounds 7 and 8), but not the negative controls (5 µM) significantly stabilized HIF1α protein (FIG. 5A) in the SH-SY5Y human neuroblastoma cell line three hours after addition of the compounds to the bathing media. Accordingly, HIF1-regulated genes such as Epo, LDHA and PGK1 (FIG. 5B) were also induced by the small molecules that stabilized HIF-1α. Interestingly, compounds 7 and 8 activated distinct patterns of HIF-dependent gene expression, suggesting that these compounds may affect distinct HIF PHD isoforms, or inhibit a single isoform to different extent. Prior studies have shown that pharmacological PHD inhibition acting specifically via inhibition of PHD1 prevents oxidative stress induced death in cortical neurons [Siddiq, A., et al., J Neurosci 29, 8828-8838 (2009)]. These results predict that compounds 7 and 8 should also protect rat cortical neurons from oxidative death. As expected from these prior findings with selective PHD inhibitors, compounds 7 and 8 show neuroprotective effects in cortical neurons stimulated to die by depletion of the versatile antioxidant glutathione (FIGS. 6A-6D). Of note, compounds 7 and 8 possess an $IC_{50}$ for neuroprotection an order of magnitude lower (0.25 µM) than those required for reporter and HIF stabilization ($IC_{50}$ of 2.0-2.5 µM). These results are consistent with a model where PHD1, which is necessary for glutathione induced oxidative death in neurons, is more sensitive to canonical PHD inhibitors than PHD2 which appears to be the dominant isoform for regulating HIF stability. Indeed, oxyquinoline and compound 10 are not only less potent HIF activators, but 20-40 times less potent as neuroprotectants (FIGS. 6A-6D). Thus, neuroprotection is exhibited in the nanomolar range only by the best hits, and, as one would predict from the reporter activation (Table in FIG. 7), compound 7 is more potent than compound 8. These results support the conclusion that structural effects play a major role in reporter activation (and HIF stabilization) rather than common iron binding potency of the studied oxyquinolines. These studies are the first to use chemical tools to validate a role for HIF PHD inhibition and not iron chelation per se in stabilizing HIF and protecting neurons from oxidative death.

Discussion of Results

Two primary modes of screening for HIF activators have been well described: a recombinant enzyme-based screen for PHD2 inhibitors [Ivan, M., et al., Proc Natl Acad Sci USA 99, 13459-13464 (2002)]; Tegley, C. M., et al., Bioorg Med Chem Lett 18, 3925-3928 (2008); Warshakoon, N.C., et al., Biorg Med. Chem. Lett. 16, 5517-5522 (2006); Warshakoon, N.C., et al., Bioorg Med Chem Lett 16, 5687-5690 (2006); Warshakoon, N.C., et al., Bioorg Med. Chem. Lett 16, 5616-5620 (2006); Warshakoon, N.C., et al., Bioorg Med. Chem. Lett 16, 5598-5601 (2006); Nangaku, M. et al., Arterioscler Thromb Vase Biol 27, 2548-2554 (2007); and compounds for enhancing hypoxia inducible factor activity and methods of use, as described in WO/2007/048004; 60/729,059].

High throughput screening for PHD inhibitors using an enzyme assay is a challenge both in terms of the enzyme source and the assay format. The enzymatic activity and stability of purified PHD is very low, and enzyme assays suitable for high content screening require large quantities of recombinant enzyme supplemented with iron. One of the challenges in the search for selective HIF PHD inhibitors or other regulators of HIF stability is to discriminate between non-specific iron chelation in solution and specific iron chelation inside the active center of the PHD enzyme. The apparent iron binding constants for the 7-branched oxyquinolines identified herein (Table in FIG. 7) are much lower than $IC_{50}$ reported for 7-linear 8-hydroxyquinoline derivatives (3-10 µM) in the PHD2 in vitro assay [Warshakoon, N.C., et al., Biorg Med. Chem. Lett. 16, 5517-5522 (2006)], which may reflect the use of excess iron in the in vitro assay mixture as compared to the instant cell based assay. Given the non-physiological conditions under which screening for inhibitors occurs with recombinant PHD2, it is not surprising that the $IC_{50}$ value determined in the enzyme in vitro assay did not correlate with the $IC_{50}$ for VEGF activation reported in the same study [Warshakoon, N.C., et al., Biorg Med. Chem. Lett. 16, 5517-5522 (2006)]. Another limitation is the use of a 19-mer HIF peptide, whose affinity for the HIF PHDs is orders of magnitude lesser than the full length protein. Studies are also being conducted to establish the affinity of the instant ODDluciferase construct (containing 128 amino acids from HIF-1α) for the HIF PHDs. A negative consequence of the test tube strategy is the assay format is more likely to yield inhibitors competitive with respect to αKG than those competing with HIF itself. The recently reported crystal structure of PHD2 with a 17-mer HIF peptide [Chowdhury, R., et al., Structure 17, 981-989 (2009)] shows no active site water displacement, which appears to be a mandatory requirement for the initiation of the catalytic cycle (see p. 277 in [Solomon, E. I., et al., Chem Rev 100, 235-350 (2000)] and [Price, J. C., et al., Biochemistry 44, 8138-8147 (2005)]). Given these biases, it is not surprising that all PHD inhibitors developed using the recombinant enzyme explored only the αKG-binding motif inside PHD2 active site and had a carboxyl group interacting with Arg-383 in addition to a clearly defined iron-binding motif [Warshakoon, N.C., et al., Biorg Med. Chem. Lett. 16, 5517-5522 (2006); Ivan, M., et al., Proc Natl Acad Sci USA 99, 13459-13464 (2002); Tegley, C. M., et al., Bioorg Med Chem Lett 18, 3925-3928 (2008); Warshakoon, N.C., et al., Bioorg Med Chem Lett 16, 5687-5690 (2006). Warshakoon, N.C., et al., Bioorg Med. Chem. Lett 16, 5616-5620 (2006); Warshakoon, N.C., et al., Bioorg Med. Chem. Lett 16, 5598-5601 (2006)].

The cell-based assay with HRE-luc reporter system, a promoter-reporter construct that contained 68 bp of a known hypoxia and HIF-1 regulated gene, enolase, containing a wild type HRE (5'-RCTGT-3'), is a widely used approach for screening of HIF activators with diverse mechanisms of action [Semenza, G. L., et al., J Biol Chem 271, 32529-32537 (1996)]. A reporter system is based on transfected immortalized hippocampal neuroblast cell line (HT22) and allows screening for a broad spectrum of compounds that include: activators of HIF transcription; activators of HIF binding to HRE; and effectors of HIF protein stability (PHD inhibitors, pVHL & proteasome inhibitors). The manual screen of Spectrum library performed in this laboratory using HRE-luc/HT22 line took half a year and resulted in 43 hits. However, in the instant study, the cell line's response to positive controls was found to be unstable over time, and after seven passages, the line had to be newly generated by transfection with the reporter plasmid. The foregoing drawbacks made the HRE-luc/HT22 line not suitable for a robotic HTS on 384-well plates.

Figure 13:
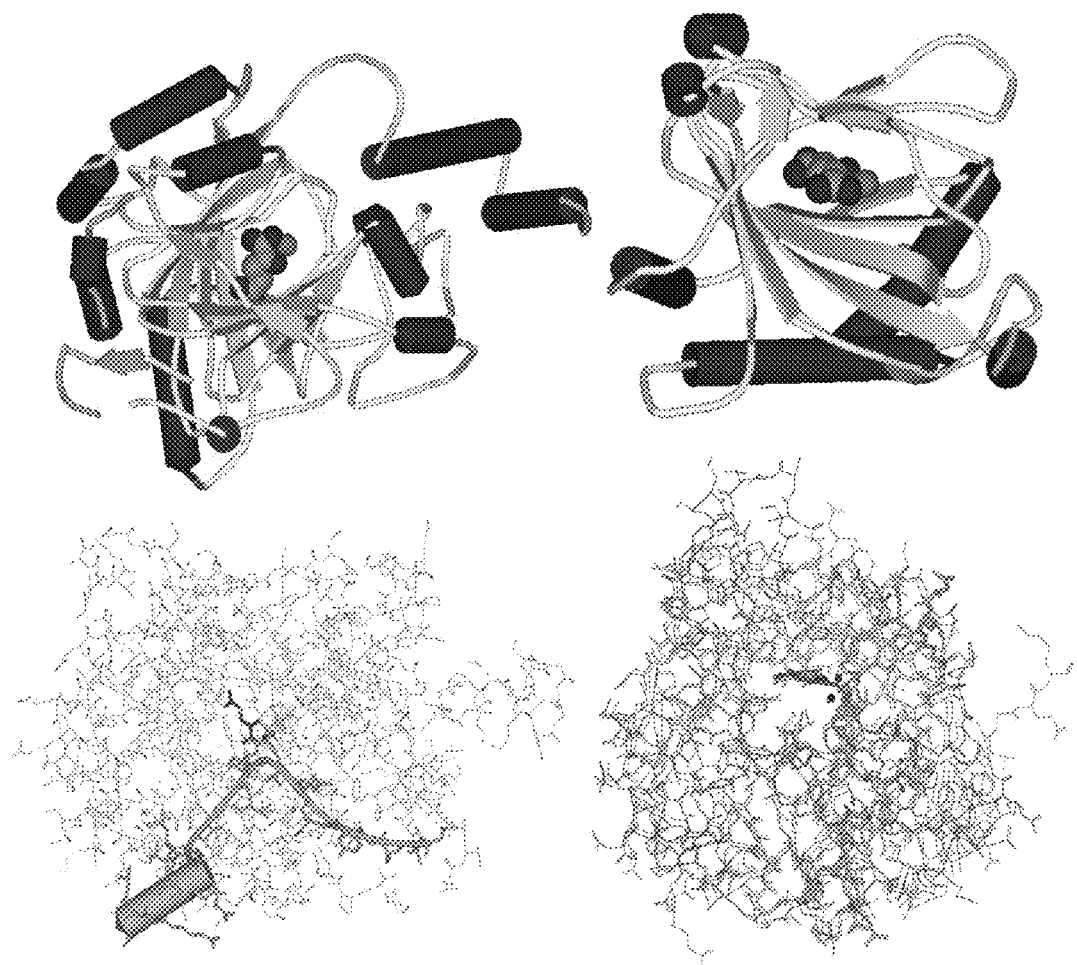
FIG. 13. FIH docking restrictions. Differences in FIH (left) and PHD2 (right) structures: view to the entrance of the active site. HIF gets access to the active site water (replaced in the course of catalysis by ferryl oxygen) in FIH from the bottom of the αKG plane, i.e. the access to the active site is perpendicular to the αKG plane, contrary to PHD2, where the access to the active site is parallel to αKG plane. This is clearly seen from the crystal structures of the enzymes in the complex with the corresponding HIF peptides. Ferryl oxygen is screened from solvent by the peptide in FIH, however, PHD2 crystal with HIF peptide shows that ferryl oxygen will be solvent accessible during the catalytic cycle, which point to the looser complex in crystal than in reality.
Figure 14:
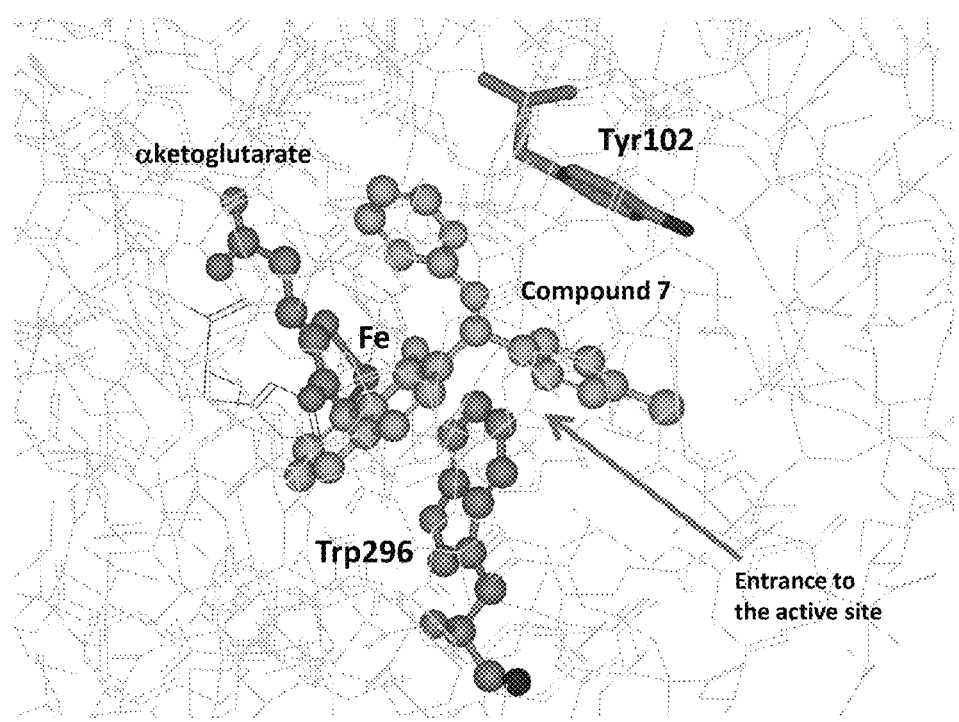
FIG. 14. FIH docking restrictions continued. Docking of branched oxyquinolines in place of αKG or in place of one αKG ligand site and active site water molecule in FIH (see below manual placement of compound 7) is not permitted. The architecture of the active site, and in particular Trp 296 and Tyr102 impose restrictions on docking bulky molecules with rigid iron binding motif and a comparatively short linker (like those found in best hits from branched oxyquinolines).
Figure 15:
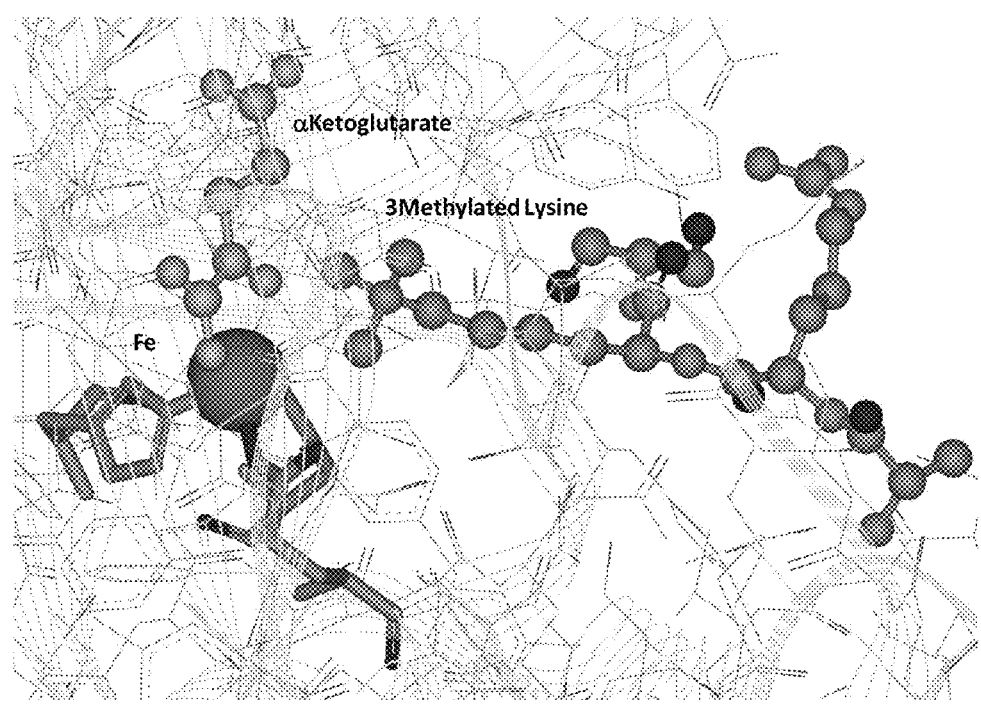
FIG. 15. Restricted access to the active site of relevant Fe-oxygenases. Jumonji histone demethylase (2Q8C.pdb) has a C7-C8 long pocket for 3-methylated lysine to reach Fe and deeply buried αKG and shows spatial restrictions for docking of bulky molecules, such as branched oxyquinolines inhibitors of PHD.
Figure 16:
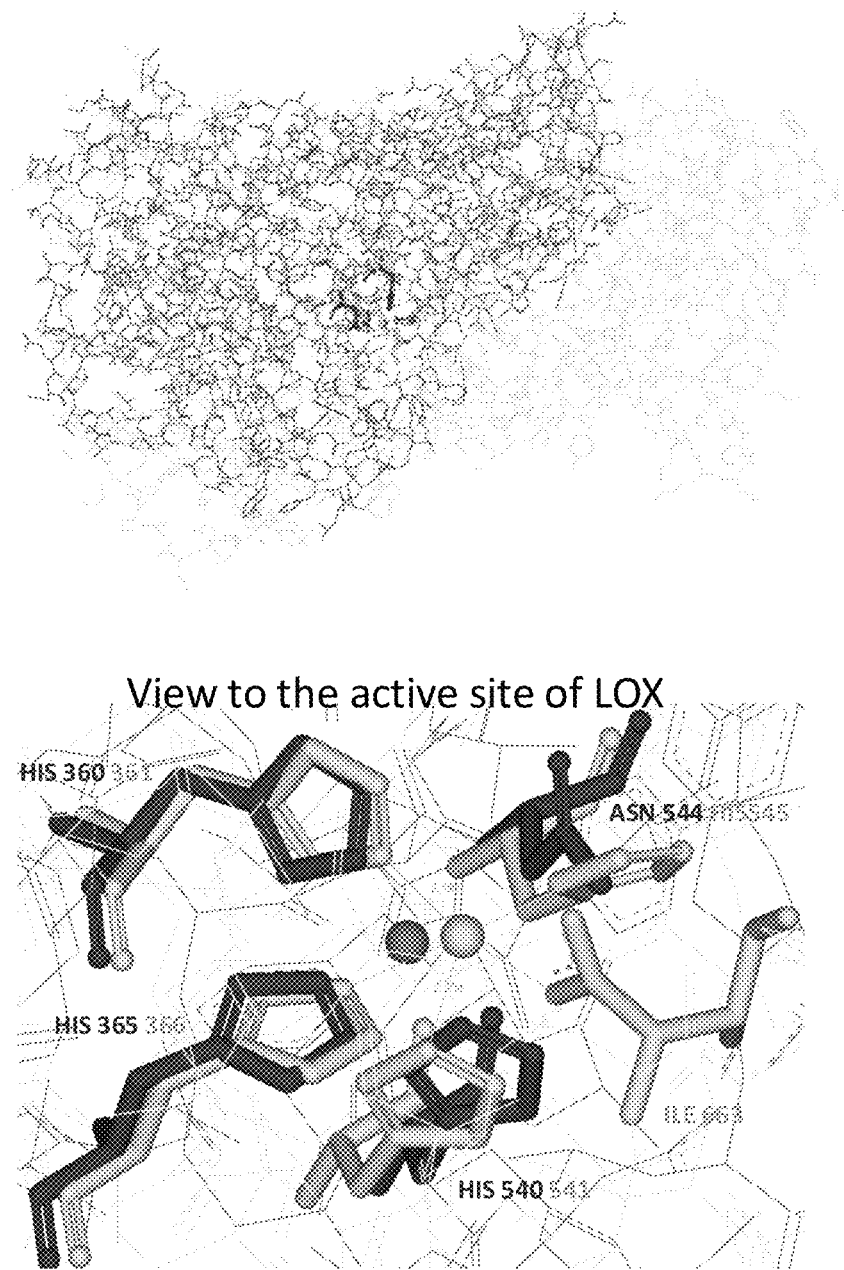
FIG. 16. Restricted access to the active site of relevant Fe-oxygenases continued. Lipoxygenase-12 active site restrictions: TOP: Overlap of human LOX-12 catalytic domain (3D3L.pdb) in purple and rabit LOX-15 (2P0M.pdb) in blue. LOX-15 has been crystallized with an inhibitor in one subunit only; the figure shows overlapped subunits containing no inhibitor. BOTTOM: Active site comparison: LOX-12 catalytic domain has been recently deposited at resolution 2.6 Å, has no coordinates for residues 599-603, and is terminated at Thr 662 (corresponds to Ile 663, the forth Fe ligand in LOX-15). LOX-12 contains Asn 544 in place of H is 545 in LOX-15. LOX-15 is known to accommodate planar inhibitors with carboxylate pointing to the iron, in place of arachidonic acid. Docking of branched oxyquinolines is impossible.
Figure 17:
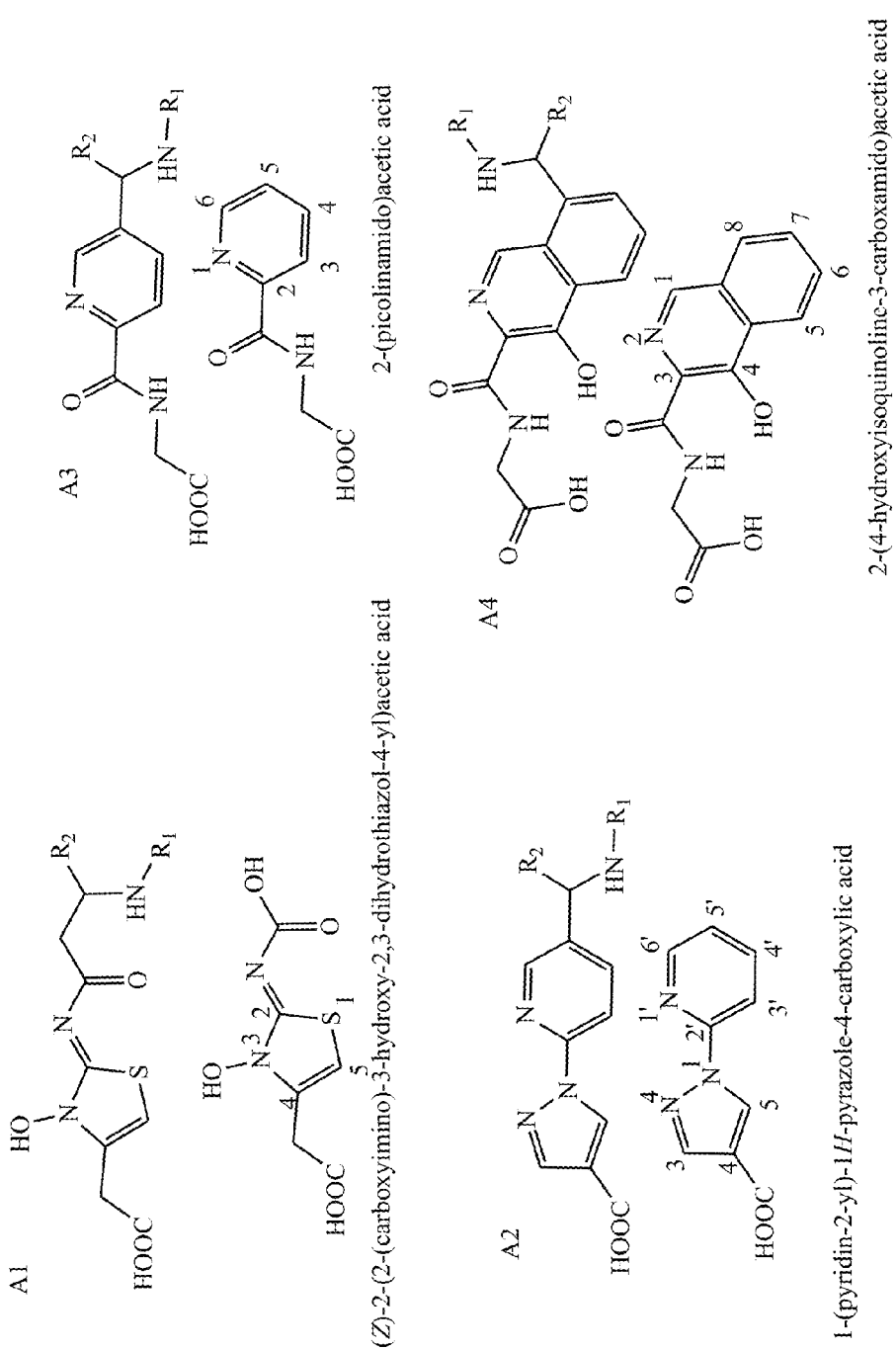
FIG. 17. Some exemplary classes of compounds of the instant invention (Groups A1-A4).
Figure 18:
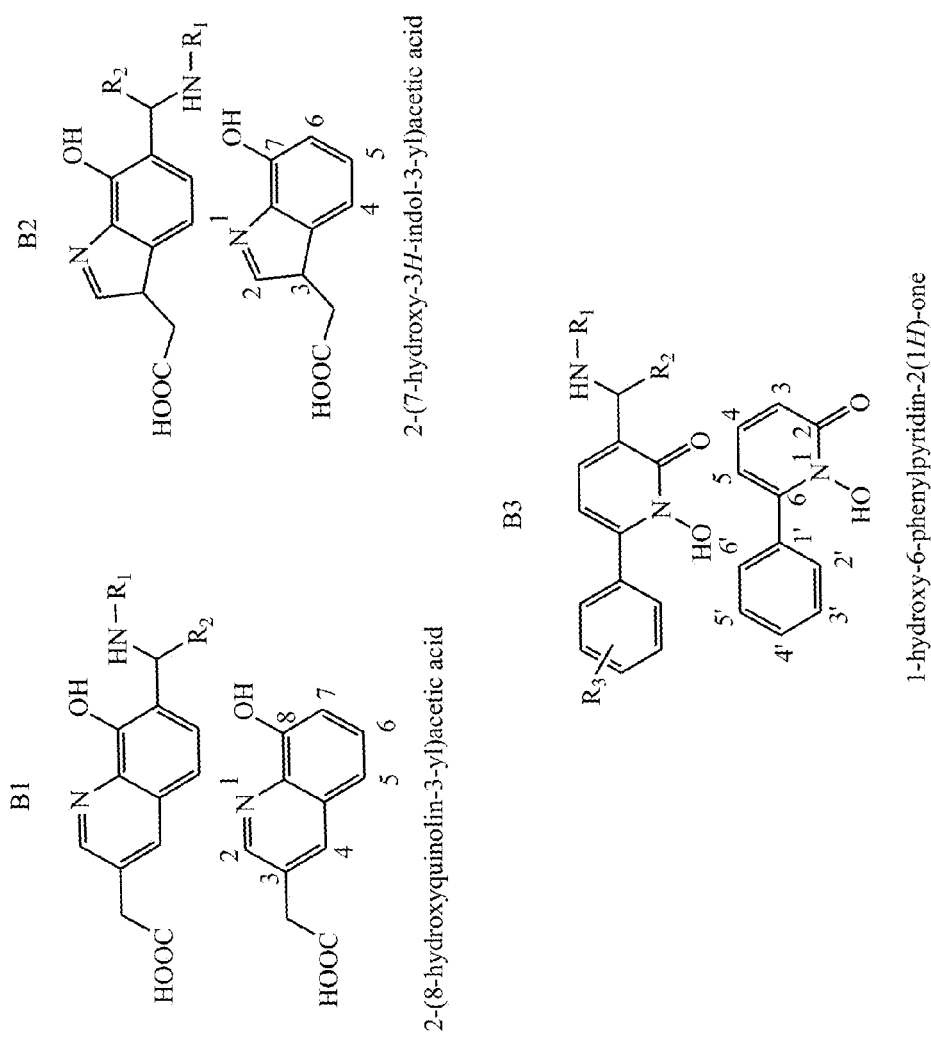
FIG. 18. Some exemplary classes of compounds of the instant invention (Groups B1-B3).
Figure 19:
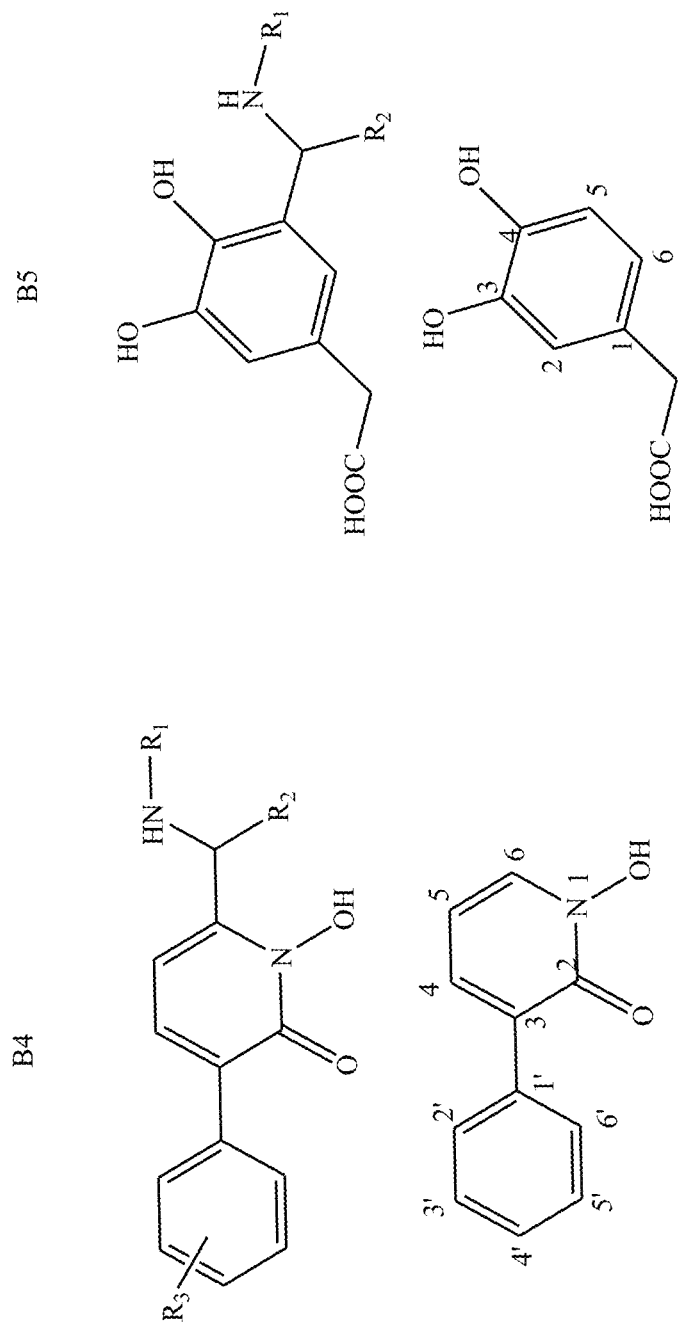
FIG. 19. Some exemplary classes of compounds of the instant invention (Groups B4 and B5).
Figure 20:
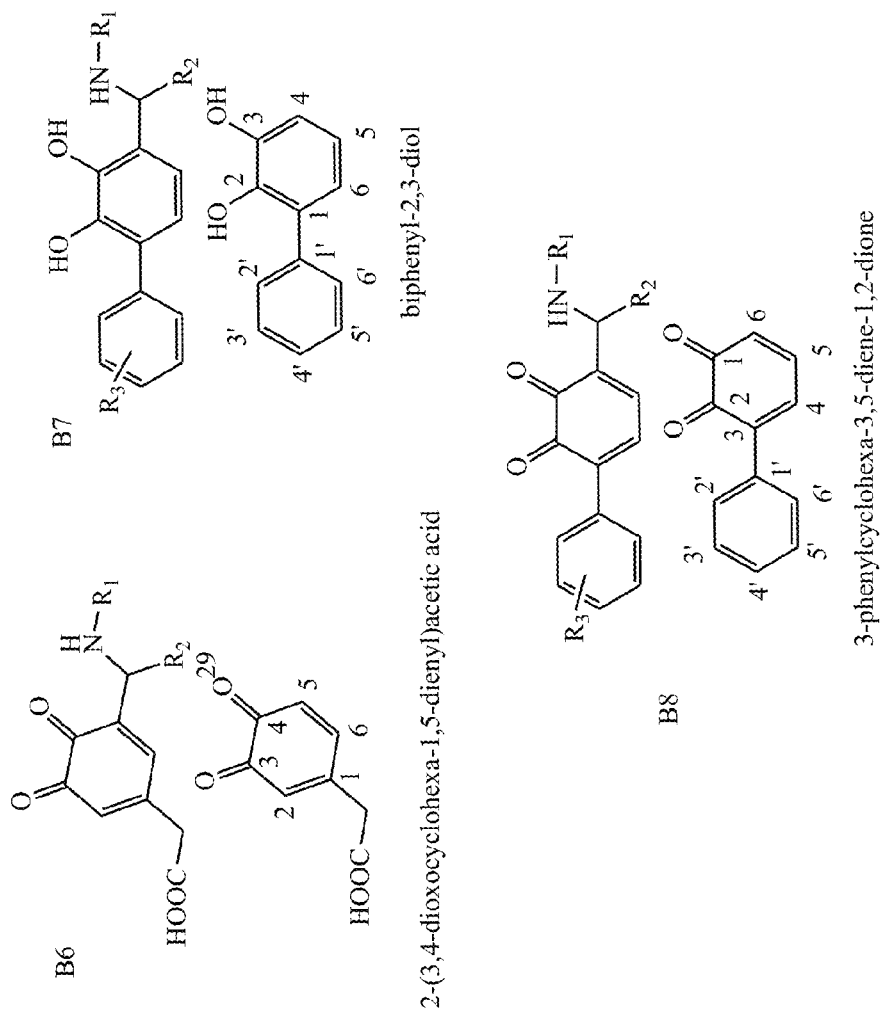
FIG. 20. Some exemplary classes of compounds of the instant invention (Groups B6-B8).
Figure 21:
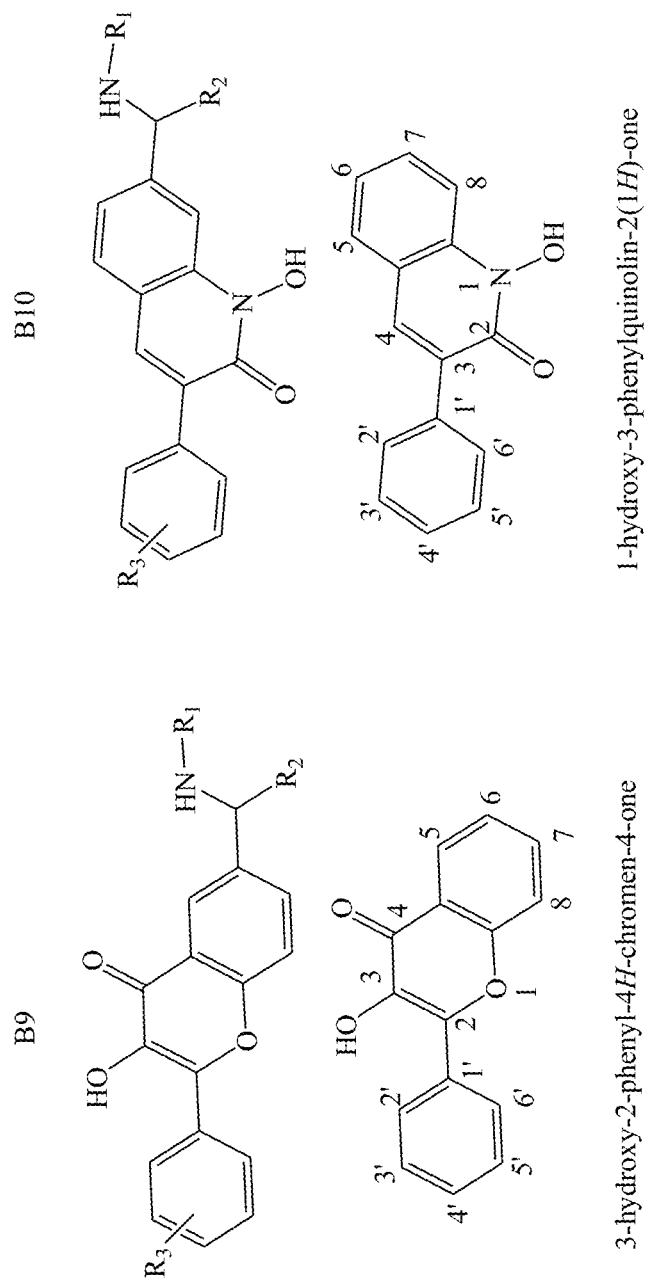
FIG. 21. Some exemplary classes of compounds of the instant invention (Groups B9 and B10).

Taking into account the low specific activity of recombinant enzymes, and the inadequacy of interpretation of the inhibition constant generated using different types of enzyme in vitro assays, a cell-based reporter system was herein developed for HTS of ODD-luc stability, a variant of the cell-based "capture" assay. A screen of 85,000 structurally diverse compounds was accomplished in less than a month. A novel, previously unknown branched structural motif was identified in the group of catechol-type and oxyquinoline hits. This suggests specific recognition by PHD among other αKG dependent Fe-dioxygenases. Comparison of crystal structures of FIH and PHD2 (FIG. 13) shows the difference in access to the active sites: PHD2 allows sliding of the αKG mimic into the active site, leaving the branched portion outside, while FIH does not. Analysis of docking modes for best hits from the HTS into the available crystal structures of αKG-dependent Fedioxygenases, e.g. FIH (FIG. 14), HIF PHD2 and jumonji demethylase (FIGS. 15-16), demonstrates that newly identified branched motifs provide specificity for HIF PHD by exploring the active site entrance, which significantly differs from those of the other enzymes of this class. In addition, these branched inhibitors did not fit into the active center of lipoxygenase-12 (FIGS. 15-16), the enzyme directly implicated into the survival mechanism in HCA model. The presence of the newly identified branched motif appears to increase the likelihood of the inhibitor specificity for HIF PHD.

Significance of Results

Brain ischemia underlies many nervous system disorders triggering a cascade of events that induce acute and delayed changes resulting in disability and cognitive decline. Over the past decade, cell adaptation to hypoxia has emerged as an active process. Although the panoply of mechanisms involved in hypoxic preconditioning are not completely understood, the discovery of HIF has opened new horizons for the treatment of ischemia. Recent evidence strongly suggests that HIF PHDs and FIH are important targets for medical intervention: small molecules that inhibit HIF PHDs are the focus of drug development efforts directed towards the treatment of ischemia in many organs, including the muscle, heart and brain. The results presented here are the first on HTS for HIF activators/HIF PHD inhibitors under the conditions most closely resembling physiological ones. In particular, the instant study has identified novel, previously undescribed branching motifs adjacent to iron-binding ligands in the group of catechol type and oxyquinoline hits. The branching motifs appear to be involved in, and have a significant impact on, the recognition by PHD. The biological effects of newly identified branched hits were in accord with their rating in HTS. Altogether, these findings validate a novel high throughput screen for small molecules that can modulate hypoxic adaptation.

Cell Lines

Human neuroblastoma SH-SY5Y cells were transfected with 1 mg of either pcDNA3-ODDLUC8 or mutant variants of this plasmid by using Lipofectamine™ 2000 (Invitrogen). Transfected cell were grown in the presence of 500 μm/ml of Genetecin (GIBCO-Invitrogen) on DMEM/F12+GlitaMAX (Dulbecco's modified Eagle medium Nutrient Mixture F-12 (Ham)(1:1) 1×, Gibco 10565) medium.

Reporter Plasmid Construction and Mutagenesis

The ODDLUC encoded plasmid pcDNA3-ODDLUC8 was constructed as described in Safran M. et al., PNAS, 2006, 103, 105-110 (2006). This plasmid was used as a template to introduce amino acid substitutions into PYIP (564-567a.a) region of HIF-ODD fragment that was suggested to determine enzyme-specific interaction of HIF-1α to three isoforms of HIF PHDs (Safran M. et al., PNAS, 2006, 103, 105-110 (2006)). The plasmids pPAIP, pPYIA and pAYIA were obtained from pcDNA3-ODDLUC8 using QuickChange Multi Site-Directed Mutagenesis kit (Agilent Technology) to introduce the corresponding mutations: Tyr565Ala, Pro567Ala, and Pro564Ala/Pro567Ala. pAYIA was used as a control line.

HTS Optimization and SAR Analysis

The assay was optimized for HTS format to provide Z values above 0.7. SH-SY5Y-ODD-luc cells were plated into 384—well white flat-bottom plates at 7,000 cell/well in 30 μl of serum and incubated overnight at 37° C., 5% $CO_2$. The next day, compounds were added to a final concentration of 10 μM, plates were incubated for three hours at 37° C., and luciferase activity was measured using SteadyGlo™ reagent (Promega). Each plate had two internal standards, ciclopirox (100%), and DMSO (0%). The reporter activation (%) was calculated as a ratio $(L-L_{DMSO})/(L_{ciclopirox}-L_{DMSO})$. Hits were defined as those >25%. HTS of 85,000 compounds was performed at Rockefeller HTS Resource Center. 295 hits from the initial screen have been tested in quadruplicate, 160 were confirmed. Classification into 10 structural clusters has been done manually; 25 hits were singletons.

Extended SAR Analysis

Oxyquinolines were purchased from ChemDiv (San Diego, Calif.) and tested in 96-format plates with varied concentrations of an inhibitor (0.05-15 μM). Cells were plated at the density of 30,000 cell per well using a WellMate multichannel dispenser from Matrix (Thermo Fisher Scientific) and grown overnight on DMEM/F12+GlitaMAX (100 μL per well), then the inhibitor was added, and the plates were incubated for a fixed time interval; the medium was removed, cells were lysed and luciferase activity was measured on a luminometer platereader Lmax11384 (Molecular Devices) with BrightGlo™ reagent (Promega). The reporter activation was normalized to the background luminescence.

HIF Immunoblot

After three hours of 5 µM drug treatment, cells were scraped in ice cold PBS and centrifuged at 1,000×g per 5 min. The pellet was used for nuclear extract preparation with the NE-PER Nuclear and Cytoplasmic Extraction kit (Pierce). After SDS-PAGE followed by transfer to a nitrocellulose membrane, the latter was incubated overnight at 4° C. with primary polyclonal antibody against HIF-1α (Upstate) and monoclonal antibody against β-actin (Sigma) (dilution 1:250 and 1:5000, respectively, in Odyssey Blocking Buffer). Secondary fluorophore conjugated Odyssey IRDye-680 and IRD-800 antibodies (LI-COR Biosciences) were added at 1:20,000 in Odyssey Blocking Buffer, and incubated for one hour at room temperature. Immunoreactive proteins were detected using Odyssey IR imaging system (LI-COR Biosciences).

Real Time-PCR

Total RNA was isolated from SH-SY5Y cells by using NucleoSpin RNAII kit (Macherey-Nagel) and was used for cDNA synthesis by SuperScript III First-Strand Synthesis System for RT-PCR (Invitrogen). Quantitative real time PCR analyses of human PHD1,2,3, LDHA, PKG1 and EPO were performed by using the corresponding primers and probe set from Applied Biosystems on the ABI 7500 Fast Real Time PCR Taqman system (Applied Biosystems). GAPDH was used for normalization.

Cell Death and Viability Assays

Primary neuronal cultures were prepared from the forebrains of Sprague-Dawley rat embryos (E17) and plated on 96 well plates at a 106 cells/ml density. After 16 hours, cells were rinsed with warm PBS and then placed in minimum Essential Medium (MEM; Life Technologies) containing 5 mM HCA in the presence of oxyquinolines (0.25-2 µM). Cells were incubated for 24 hours or longer until 90% cell death in HCA treated controls. Viability was assessed by the MTT (4,5-dimethylthiazol-2-yl)-2,5-diphenyltetrazolium bromide) assay [Mosmann, T., J Immunol Methods 65, 55-63 (1983)].

Iron Binding Properties of Oxyquinolines

The iron chelation ability is determined by displacement of calcein from its complex with iron monitored by fluorescence (excitation 490 nm, emission 523 nm, cut-off 515 nm) on a Spectramax M5e platereader (Molecular Devices). The apparent binding constant for calcein (ca.50 nM) was determined from Fe titration curve for 1 µM calcein in 5 mM Tris-HCl buffer, pH 7.5. The ratio between the iron binding constant for calcein and a particular compound, i.e., $K_Q/K_{Ca}$, was estimated by fitting the titration curve into the dependence of $[Fe]_o$ vs. Y, where Y=[Ca—Fe]/[Ca] is a ratio of calcein-bound Fe to free (fluorescent) calcein:

$$[Fe]o=K_{Ca}Y+[Ca]oY/(Y+1)+[Q]oY/(Y+K_Q/K_{Ca}) \quad \text{(Eq.4)}$$

The association rate constant was determined as the second order rate constant for calcein displacement from its complex with iron (1 µM:1 µM) upon addition of an oxyquinoline (5-20 µM) calculated from the slope of a linear plot of the initial rate of calcein release vs. the concentration of oxyquinoline added. All experiments were performed in triplicates or more. All values are presented as mean±S.E.M.

Computer Modeling

Docking simulation experiments were performed using the CDOCKER algorithm [Wu, G., et al (2003)] as implemented in the Discovery studio 2.5 software suite (Accelrys, San Diego, Calif.), followed by force field minimization and binding energy calculations using the PHD2 crystal structure with the bound inhibitor (2G19.pdb) as the starting template structure. Preparation of the receptor was achieved by running a protein check and identifying all the elements of the structure. It was noted that there were amino acids missing on the N-terminus and C-terminus; however, these were not in close proximity to the binding site, and therefore, there was no need to add them to the structure. Force field minimization was conducted using the molecular mechanics algorithm CHARMm [Brooks, B. R., et al., J. Comput. Chem. 4, 187-217 (1983)] as implemented in Discovery Studio 2.5.

While there have been shown and described what are at present considered the preferred embodiments of the invention, those skilled in the art may make various changes and modifications which remain within the scope of the invention defined by the appended claims.

What is claimed is:

1. A method for treating a patient having brain ischemia, the method comprising administering to said patient in need thereof an effective amount of a HIF prolyl-4-hydroxylase inhibiting compound within the following general formula:

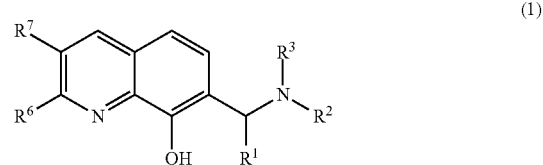

(1)

wherein:

$R^1$ is a monocyclic group, wherein said monocyclic group is optionally substituted with one or more groups selected from —$R^4$, —C(O)$R^4$, —N$R^4_2$, —OR4, NO$_2$, —C(O)N$R^4_2$, —N$R^4$C(O)$R^4$, —C(O)O$R^4$, —N$R^4$C(O)N$R^4_2$, —N$R^4$C(O)O$R^4$, —SO$_2R^4$, nitrile, and halogen atom, wherein $R^4$ is, independently, hydrogen atom or a non-cyclic hydrocarbon group containing up to nine carbon atoms; and/or said monocyclic group is optionally substituted with one or more linkers linking the monocyclic group with the shown carbon atom, wherein said linker is selected from —R4-, —C(O)—, —C(0)R4-, —N$R^4$—, —C=N$R^4$—, —N=N$R^4$—, —C=N$R^4$—, —C=N—N$R^4$, —O—, —S—, —C(O)N$R^4$—, —N$R^4$C(O)$R^4$—, —C(O)O—, —C(O)O$R^4$—, —N$R^4$C(O)N$R^4$—, —N$R^4$C(O)O$R^4$—, —SO$_2R^4$—, and combinations thereof;

$R^2$ is selected from unsaturated monocyclic heterocyclic ring containing one or more ring-heteroatoms selected from nitrogen, oxygen, and sulfur, and/or one or more ring functional groups selected from —C(O)— and —C(S)—, wherein said unsaturated monocyclic heterocyclic ring is substituted with an —OH group and optionally further substituted with one or more groups selected from —$R^4$, —C(O)$R^4$, —N$R^4_2$, —O$R^4$, —NO$_2$, —C(O)N$R^4_2$, —N$R^4$C(O)$R^4$, —C(O)O$R^4$, —N$R^4$C(O)N$R^4_2$, —N$R^4$C(O)O$R^4$—, —SO$_2R^4$—, nitrile, and halogen atom, and wherein said unsaturated monocyclic heterocyclic ring is either directly bound or indirectly bound via one or more linkers to the shown nitrogen atom, wherein said linker is selected from —$R^4$—, —N$R^4$—, —C=N$R^4$—, —N=N$R^4$—, —ON$R^4$—, —C=N—NR4-, —O—, —S—, —C(O)N$R^4$—, —N$R^4$C(O)$R^4$—, —C(O)O—, —C(O)O$R^4$—, —N$R^4$C(O)N$R^4$—, —N$R^4$C(O)O$R^4$—, —S0$_2R^4$—, and combinations thereof;

$R^3$ is selected from hydrogen atom and hydrocarbon group containing up to six carbon atoms;

and R6 and R7 are independently selected from hydrogen atom, hydrocarbon groups containing up to three carbon atoms, and polar groups and methylene-linked versions thereof, wherein the 8-OH group shown in said structural formula can optionally have the hydrogen atom absent and the oxygen atom instead linked with $R^3$ to form a cyclic ether.

2. The method of claim 1, wherein $R^1$ is a phenyl ring optionally substituted with one or more groups selected from —$R^4$, —$C(O)R^4$, —$NR^4{}_2$, —$OR^4$, $NO_2$, —$C(O)NR^4{}_2$, —$NR^4C(O)R^4$, —$C(O)OR^4$, —$NR^4C(O)NR^4{}_2$, —$NR^4C(O)OR^4$, —$SO_2R^4$, nitrile, and halogen atom, wherein $R^4$ is as defined in claim 1.

3. The method of claim 1, wherein $R^1$ is a phenyl ring substituted with at least one polar group selected from hydroxy, carboxy, methoxy, ethoxy, propoxy, isopropoxy, halogen atom, —$NH_2$, nitro, and ammonium groups.

4. The method of claim 1, wherein $R^1$ is a monocyclic aromatic or heteroaromatic group, wherein said heteroaromatic group contains at least one ring heteroatom selected from nitrogen, oxygen, and sulfur.

5. The method of claim 1, wherein the unsaturated monocyclic ring of $R^2$ is directly bound to the shown nitrogen atom.

6. The method of claim 1, wherein said unsaturated monocyclic heterocyclic ring under $R^2$ contains at least one nitrogen ring atom.

7. The method of claim 1, wherein said unsaturated monocyclic heterocyclic ring under $R^2$ is a pyridyl ring.

* * * * *